US011891347B2

(12) United States Patent
Mukherjee et al.

(10) Patent No.: US 11,891,347 B2
(45) Date of Patent: Feb. 6, 2024

(54) CATALYZED ALKYLATION, ALKYLATION CATALYSTS, AND METHODS OF MAKING ALKYLATION CATALYSTS

(71) Applicant: Exelus Inc., Fairfield, NJ (US)

(72) Inventors: Mitrajit Mukherjee, Livingston, NJ (US); Eric Daniel Gauthier, Succasunna, NJ (US); Kelly Ann Coley, Warren, NJ (US)

(73) Assignee: Exelus Inc., Fairfield, NJ (US)

( * ) Notice: Subject to any disclaimer, the term of this patent is extended or adjusted under 35 U.S.C. 154(b) by 0 days.

(21) Appl. No.: 17/584,610

(22) Filed: Jan. 26, 2022

(65) Prior Publication Data
US 2022/0144724 A1 May 12, 2022

Related U.S. Application Data

(62) Division of application No. 16/590,328, filed on Oct. 1, 2019, now Pat. No. 11,261,139, which is a division
(Continued)

(51) Int. Cl.
| | |
|---|---|
| B01J 29/06 | (2006.01) |
| C07C 2/58 | (2006.01) |
| B01J 29/08 | (2006.01) |
| B01J 29/70 | (2006.01) |
| B01J 37/30 | (2006.01) |
| B01J 37/02 | (2006.01) |
| C01B 39/20 | (2006.01) |
| C01B 39/02 | (2006.01) |
| C01B 39/46 | (2006.01) |
| C10G 29/20 | (2006.01) |
| B01J 29/90 | (2006.01) |
| B01J 29/12 | (2006.01) |

(Continued)

(52) U.S. Cl.
CPC ................ *C07C 2/58* (2013.01); *B01J 29/08* (2013.01); *B01J 29/082* (2013.01); *B01J 29/084* (2013.01); *B01J 29/087* (2013.01); *B01J 29/088* (2013.01); *B01J 29/123* (2013.01); *B01J 29/126* (2013.01); *B01J 29/143* (2013.01); *B01J 29/7007* (2013.01); *B01J 29/7057* (2013.01); *B01J 29/7407* (2013.01); *B01J 29/90* (2013.01); *B01J 37/0201* (2013.01); *B01J 37/024* (2013.01); *B01J 37/08* (2013.01); *B01J 37/30* (2013.01); *B01J 38/10* (2013.01); *C01B 39/026* (2013.01); *C01B 39/20* (2013.01); *C01B 39/46* (2013.01); *C07C 2/54* (2013.01); *C07C 2/56* (2013.01); *C07C 9/14* (2013.01); *C07C 9/16* (2013.01); *C10G 29/205* (2013.01); *B01J 2229/10* (2013.01); *B01J 2229/18* (2013.01); *B01J 2229/186* (2013.01); *B01J 2229/20* (2013.01); *B01J 2229/40* (2013.01); *C07C 2529/08* (2013.01); *C07C 2529/12* (2013.01); *C07C 2529/14* (2013.01); *C07C 2529/70* (2013.01); *C10G 99/00* (2013.01); *C10G 2300/104* (2013.01); *C10G 2300/1081* (2013.01); *C10G 2300/1092* (2013.01); *C10G 2300/305* (2013.01); *C10G 2300/70* (2013.01); *C10G 2400/02* (2013.01); *Y02P 20/584* (2015.11)

(58) Field of Classification Search
CPC ........ B01J 38/10; B01J 29/082; B01J 29/084; B01J 29/085; B01J 29/08; B01J 29/087; B01J 29/088; B01J 29/123; B01J 29/126; B01J 29/143; B01J 29/7007; B01J 29/7057; B01J 29/7407; B01J 29/90; B01J 2229/10; B01J 2229/18; B01J 2229/186; B01J 2229/20; B01J 2229/40; B01J 37/0201; B01J 37/024; B01J 37/08; B01J 37/30; C01B 39/026; C01B 39/20; C01B 39/46; C07C 2529/08; C07C 2529/12; C07C 2529/14; C07C 2529/70; C10G 2300/70; C10G 2300/305; C10G 2300/1092; C10G 2300/1081; C10G 2300/104
USPC ....................... 502/60, 79; 423/700
See application file for complete search history.

(56) References Cited

U.S. PATENT DOCUMENTS

| | | | |
|---|---|---|---|
| 3,293,192 A | 12/1966 | Maher et al. | |
| 3,832,970 A | 9/1974 | Nillson | |

(Continued)

FOREIGN PATENT DOCUMENTS

| | | |
|---|---|---|
| CN | 102191081 B | 4/2014 |
| WO | 1997020787 A1 | 6/1997 |

OTHER PUBLICATIONS

Office Action in Canadian Application No. CA2989428A dated Dec. 16, 2022.
(Continued)

*Primary Examiner* — Elizabeth D Wood
(74) *Attorney, Agent, or Firm* — Frank Rosenberg

(57) ABSTRACT

Improved alkylation catalysts, alkylation methods, and methods of making alkylation catalysts are described. The alkylation method comprises reaction over a solid acid, zeolite-based catalyst and can be conducted for relatively long periods at steady state conditions. The alkylation catalyst comprises a crystalline zeolite structure, a Si/Al molar ratio of 20 or less, less than 0.5 weight percent alkali metals, and further having a characteristic catalyst life property. Some catalysts may contain rare earth elements in the range of 10 to 35 wt %. One method of making a catalyst includes a calcination step following exchange of the rare earth element(s) conducted at a temperature of at least 575° C. to stabilize the resulting structure followed by an deammoniation treatment. An improved method of deammoniation uses low temperature oxidation.

9 Claims, 11 Drawing Sheets

Related U.S. Application Data of application No. 15/190,063, filed on Jun. 22, 2016, now Pat. No. 10,464,863.

(60) Provisional application No. 62/183,037, filed on Jun. 22, 2015.

(51) Int. Cl.

| | | |
|---|---|---|
| B01J 38/10 | (2006.01) | |
| B01J 29/74 | (2006.01) | |
| C07C 2/56 | (2006.01) | |
| C07C 2/54 | (2006.01) | |
| C07C 9/14 | (2006.01) | |
| C07C 9/16 | (2006.01) | |
| B01J 29/14 | (2006.01) | |
| B01J 37/08 | (2006.01) | |
| C10G 99/00 | (2006.01) | |

(56) References Cited

U.S. PATENT DOCUMENTS

| | | |
|---|---|---|
| 3,851,004 A | 11/1974 | Yang |
| 3,893,942 A | 7/1975 | Yang |
| 3,917,738 A | 11/1975 | Fenske et al. |
| 4,116,880 A | 9/1978 | Olah |
| 4,384,161 A | 5/1983 | Huang |
| 4,683,214 A | 7/1987 | Angevine et al. |
| 4,992,615 A | 2/1991 | Huss, Jr. et al. |
| 5,012,033 A | 4/1991 | Child et al. |
| 5,120,897 A | 6/1992 | Del Rossi et al. |
| 5,157,196 A | 10/1992 | Crossland et al. |
| 5,157,197 A | 10/1992 | Cooper et al. |
| 5,190,904 A | 3/1993 | Crossland et al. |
| 5,220,095 A | 6/1993 | Homeltoft, et al. |
| 5,221,777 A | 6/1993 | Huss, Jr. et al. |
| 5,245,101 A | 6/1993 | Del Rossi et al. |
| 5,237,120 A | 8/1993 | Haag et al. |
| 5,279,726 A | 1/1994 | Nard |
| 5,288,685 A | 2/1994 | Kellenbach et al. |
| 5,324,881 A | 6/1994 | Kresge et al. |
| 5,346,676 A | 9/1994 | Crossland et al. |
| 5,364,976 A | 11/1994 | Kallenbach |
| 5,391,527 A | 2/1995 | Kojima et al. |
| 5,475,178 A | 12/1995 | Del Rossi et al. |
| 5,489,729 A | 2/1996 | Benazzi et al. |
| 5,675,053 A | 10/1997 | Hommeltot |
| 5,731,256 A | 3/1998 | Benazzi et al. |
| 5,739,074 A | 4/1998 | Kocal et al. |
| 5,856,588 A | 1/1999 | Pei-Shing et al. |
| 5,986,158 A | 11/1999 | Van Broekhoven et al. |
| 6,004,527 A | 12/1999 | Murrell et al. |
| 6,844,479 B2 | 1/2005 | Yeh et al. |
| 7,459,412 B2 | 12/2008 | Lercher et al. |
| 7,495,143 B2 | 2/2009 | Gao et al. |
| 7,510,644 B2 | 3/2009 | Overbeek et al. |
| 8,940,652 B2 | 1/2015 | Fu et al. |
| 9,446,960 B2 | 9/2016 | Luyken et al. |
| 9,840,422 B2 | 12/2017 | Gao et al. |
| 2009/0275791 A1 | 11/2009 | Ercan |

OTHER PUBLICATIONS

Chen, Jinwu, "Catalytic Cracking Process and Engineering", China Petrochemical Press, p. 193-194, 2005 (no English translation available).
2nd Office Action from National Institute of Industrial Property of Brazil for Application No. BR112017027823.5 dated Apr. 20, 2021.
Translation of 2nd Office Action from National Institute of Industrial Property of Brazil for Application No. BR112017027823.5 dated Apr. 20, 2021.
Search Opinion from European Application 20177177.1 dated Jan. 15, 2021.
Search Report from European Application 20177177.1 dated Jan. 15, 2021.
2nd Office Action for Chinese application 201680036871.6 dated Apr. 6, 2021.
Translation of 2nd Office Action for Chinese application 201680036871.6 dated Apr. 6, 2021.
3rd Office Action from National Institute of Industrial Property of Brazil for Application No. BR112017027823.5 published Oct. 5, 2021.
Translation of 3rd Office Action from National Institute of Industrial Property of Brazil for Application No. BR112017027823.5 published Oct. 5, 2021.
Guzman, Alexander, et al., "Influence of the activation temperature on the physicochemical properties and catalytic Activity of La-X zeolites for isobutane/cis-2-butene alkylation", Microporous and Mesoporous Materials 97 (2006) 49-57.
Kunkeler, P.J. et al., "Zeolite Beta: The Relationship between Calcination Procedure, Aluminum Configuration, and Lewis Acidity", Journal of Catalysis 180, 234-244 (1988).
Rørvik, Tine, et al.,, "Isbutane/2-butene alkylation on fresh and regenerated La-EMT-51 compared with H-EMT. The catalysts selectivity changes at high butene conversion in a slurry reactor", Applied Catalysis A: General 156 (1997) 267-283.
Schüßler, Florian et al., "Nature and Location of Cationic Lanthanum Species in High Alumina Containing Faujasite type Zeolites", The Journal of Physical Chemistry C, (2011) 115(44), 21763-21776.
Linde Molecular Sieves, Catalyst Bulletin, "Ion Exchange and Metal-Loading Procedures", Union Carbide, published prior to 2015.
Linde Molecular Sieve, Catalysts, "A Report on Molecular Sieve Catalyst SK-500", Union Carbide, published prior to 2015.
Costa, B.O. Dalla, "Isobutane alkylation with solid catalysts based on beta zeolite", Applied Catalysis A: General 385 (2010) 144-152.
Lutz, W., et al. "Investigations of the Mechanism of Dealumination of Zeolite Y by Steam: Tuned Mesopore Formation Versus the Si/Al Ratio", Studies in Surface Science and Catalysis, vol. 154, Part B, 2004, pp. 1411-1417.
Monsalve, "Active Acid Sites in Zeolite Catalyzed Iso-butanelcis-2-Butene Alkylation". (Doctoral Dissertation, Technical University of Munich), 2004.
Nayak, Vikram S. et al., "Acid Strength Distribution and Catalytic Properties of H-ZSM-5: Effect of Deammoniation Conditions of NH4-ZSM-5", Journal of Catalysis 81, 26-45 (1983).
Schüßler, Florian et al., Enhancement of Dehydrogenation and Hydride Transfer by La3+ Cations in Zeolites during Acid Catalyzed Alkane Reactions, ACS Catalysis, 2014, 4(6). pp. 1743-1752.
Zuazo, Iker, "Deactivation Routes in Zeolite Catalyzed Isobutane/2-Butene Alkylation and Regeneration Procedures", Doctoral Dissertation, Technical University of Munich, 2004.
International Search Report from International Application PCT/US2016/038827 dated Mar. 13, 2017.
Written Opinion from International Application PCT/US2016/038827 dated Mar. 13, 2017.
International Preliminary Examination Report for PCT/US2016/038827 dated Jan. 4, 2018.
National institute of Industrial Property of Brazil Search Report and Office Action for Application No. BR112017027823-5 dated Feb. 10, 2020.
European Patent Office Communication pursuant to Article 94(3) EPC for Application No. EP16738264.7 dated Jul. 3, 2019.
Intellectual Property India Examination Report for Application No. 201837002138 dated Nov. 29, 2019.
U.S. Pat. No. 392,133, Issue date Oct. 30, 1888, Peck, Eugene H. Oct. 30, 1888 (Note: Current Electronic IDS form will not accept old patent numbers).
Machine translation of description of Chinese Patent CN 102191081 B.
Klingmann et al., "Hydrogenative regeneration of a Pt/La-Y zeolite catalyst deactivated in the isobutane/n-butene alkylation", Applied Catalysis A: General, 2005, vol. 281, pp. 215-223, Elsevier.
First Office Action and Search Report for Chinese Application No. 201680036871.6, dated Apr. 17, 2020.

(56) References Cited

OTHER PUBLICATIONS

Translation of First Office Action and Search Report for Chinese Application No. 201680036871.6 dated Apr. 17, 2020.
First Office Action in Korean Application No. KR1020187000043A dated Nov. 10, 2022.
Translation of First Office Action in Korean Application No. KR1020187000043A dated Nov. 10, 2022.

dT/dP > 10

L/dP > 50

CATALYZED ALKYLATION, ALKYLATION CATALYSTS, AND METHODS OF MAKING ALKYLATION CATALYSTS

RELATED APPLICATION

This application is a divisional of U.S. patent application Ser. No. 16/590,328, filed 1 Oct. 2019, now U.S. Pat. No. 11,261,139, which is a divisional of U.S. patent application Ser. No. 15/190,063 filed 22 Jun. 2016, now U.S. Pat. No. 10,464,863, and claims the priority benefit of U.S. Provisional Patent Application Ser. No. 62/183,037, filed 22 Jun. 2015.

INTRODUCTION

The term "alkylate" refers to the reaction product of isobutane with olefins. High-octane alkylate is the cleanest gasoline blending stream produced in a refinery. Alkylate is an ideal clean fuel component because pollution from alkylate is low and alkylate has low toxicity. Alkylate has been blended into gasoline for decades to improve octane and thus the antiknock properties of gasoline. Alkylate's importance to refiners continues to grow. It makes up about 13%, or more than 12 million barrels per day, of current North American fuel. For the refiner striving to meet the stricter motor fuel specifications being mandated on an expanding worldwide basis, investment in alkylation capacity can lead to enhanced refinery flexibility and profitability. Alkylate is made currently using liquid acid catalysts. Refiners typically use either hydrofluoric acid (HF), which can be deadly if spilled, or sulfuric acid ($H_2SO_4$), which also potentially is harmful and increasingly costly to recycle.

In an alkylation reaction, light olefins are reacted with iso-paraffins (typically iso-butane) in the presence of a strong acid catalyst. The alkylation of isobutane with $C_2$-$C_5$ olefins involves a series of consecutive and simultaneous reactions occurring through carbocation intermediates. The first step is the addition of a proton to the isobutane to form a tert-butyl, or t-butyl cation. The t-butyl cation then is added to an olefin to give the corresponding $C_8$ carbocation. These $C_8$ carbocations may isomerize via hydride transfer and methyl shifts to form more stable cations. Then the $C_8$ cations undergo rapid hydride transfer with isobutane, to form the desired iso-octane molecule, and the t-butyl cation is regenerated to perpetuate the chain sequence.

Unfortunately, these are not the only reactions occurring during alkylation. There are a number of secondary reactions that, in general, tend to reduce the quality of the alkylate. Polymerization results from the addition of a second olefin to the $C_8$+ cation formed in the primary reaction, thereby forming cations with more than 8 carbon atoms, such as $C_{12}$+ cations. The $C_{12}$+ cation can continue to react with an olefin to form a larger cation. The successive addition of olefins to carbocations, or olefin polymerization, is believed generally to be the primary route to catalyst deactivation. The olefin addition reaction sometimes is referred to as a polymerization step, while the hydride-transfer reaction is denoted as the main alkylation reaction. The polymerization reaction results in the formation of "coke". The heavier alkylate molecules can then crack over the acid sites to form lighter $C_5$-$C_7$ hydrocarbons. As a result, alkylate consists of paraffinic molecules from light iso-pentane ($C_5H_{12}$) to heavier ($C_{12}H_{26}$ and larger) hydrocarbons.

Solid acid catalysts have been investigated as alternatives to liquid catalysts for nearly 30 years. Some of these catalysts include $AlCl_3$; platinum compounds; heteropolyacids, such as tungstates; and liquid acids immobilized on silica, polymers, or other solid supports. Natural or artificial zeolites also have been used. Solid acid catalysts can be tuned to improve selectivity and reduce production costs, but they tend to deactivate rapidly under alkylation reaction conditions through two mechanisms: 1) "Coke" formation on active sites from olefin polymerization reaction and 2) Pore-mouth plugging by heavy alkylate molecules The heavy hydrocarbons tend to plug the pore structure of solid catalysts, thereby reducing access to acidic sites.

There has been great interest in developing improved solid acid alkylation catalysts. For example, Japanese Patent Application No. 1-245853, U.S. Pat. Nos. 3,962,133 and 4,116,880, and United Kingdom Patent Nos. 1,432,720 and 1,389,237, disclose $H_2SO_4$ enhanced super acid catalysts; U.S. Pat. Nos. 5,220,095, 5,731,256, 5,489,729, 5,364,976, 5,288,685 and European Patent Application No. 714,871A, disclose $CF_3SO_3H$/silica catalysts; U.S. Pat. Nos. 5,391,527, and 5,739,074, disclose Pt—$AlCl_3$—$KCl/Al_2O_3$ catalysts; U.S. Pat. Nos. 5,157,196, 5,190,904, 5,346,676, 5,221,777, 5,120,897, 5,245,101, 5,012,033, 5,157,197, and published PCT Application No. WO 95/126,815, etc. disclose Lewis acid catalysts, such as $SbF_5$, $BF_3$ and $AlCl_3$; U.S. Pat. Nos. 5,324,881, and 5,475,178, disclose supported heteropolyacid catalysts; U.S. Pat. Nos. 3,917,738 and 4,384,161, disclose molecular sieve catalysts. Nonetheless, despite continued efforts over 50 years, there is still an unmet need for an improved, stable and economical solid acid alkylation catalyst.

Solid acid catalysts, such as zeolite catalysts that have a plurality of $H^+$, or acid sites, which are less toxic and less dangerous; however, such catalysts have fewer $H^+$, or acid sites than liquid acid catalysts, and only a portion of such acid sites are strong enough to catalyze alkylation reactions. Fundamentally different from liquid acids, zeolites have different populations of sites which differ substantially in their nature (Bronsted vs Lewis acids) and strength. Depending on the type of zeolite, its aluminum content, and the exchange procedure, Brønsted and Lewis acid sites having a wide range of strength and concentration are present. Zeolites exhibit a considerably lower proton (acid site) concentration than liquid acids. For example, 1 g of $H_2SO_4$ contains $20 \times 10^{-3}$ moles of protons, whereas 1 g of zeolite HY, with a Si/Al ratio of five, contain no more than $1 \times 10^{-3}$ moles of protons out of which 20-30% are strong enough to catalyze the alkylation reaction. As a result, the useful lifetime of a solid-acid catalyst is usually 2 orders of magnitude shorter than a liquid acid catalyst making it difficult to develop commercially viable paraffin alkylation technologies using solid-acid catalysts.

Methods of making zeolite catalysts having improved characteristics for alkylation have been described by Lercher et al. in U.S. Pat. No. 7,459,412. The catalysts described in this patent contain a crystalline zeolite with a silica ($SiO_2$) to Alumina ($Al_2O_3$) molar ratio less than 10, and an alkali metal content of 0.2 wt % or less. In the examples, Lercher et al. treated a commercial zeolite X with lanthanum nitrate, and then ammonium nitrate, and calcined at 450° C. in flowing air to result in the low alkali metal content zeolite catalyst. Lercher et al. reported that the catalyst should have the highest possible concentration of Bronsted acid centers and a low concentration of strong Lewis acid centers. The Lewis acid centers are catalytically inactive, but bind olefins that accelerate oligomerization and deactivation of the catalyst. Lercher et al. report that the Lewis acid centers arise from aluminum cations that are released from the crystal lattice during the calcination step.

Prior art methods that do not combine the rare earth treatments with deammoniation have described deammoniation temperatures of at least 500° C. See U.S. Pat. Nos. 3,893,942, 3,851,004, and 5,986,158.

The release of aluminum from the zeolite crystal lattice is known as dealumination and occurs at elevated temperature in the presence water vapor. For example, Lutz et al. in "Investigations of the Mechanism of Dealumination of Zeolite Y by Steam: Tuned Mesopore Formation Versus the Si/Al Ratio," in the Proceedings of the $14^{th}$ Int'l Zeolite Conf., pp. 25-30 (2004) reported on the dealumination of zeolite Y at 1 bar water vapor at 500° C., 600° C., and 700° C. showing increasing rates of dealumination with increasing temperature.

SUMMARY OF THE INVENTION

In a first aspect, the invention provides method of alkylating isobutane, comprising: under steady state conditions, passing a feed mixture of isobutane and C2-05 olefins (which is typically conducted in a continuous fashion) into a reaction chamber such that catalyst age is 2.5 or greater and producing 5 kg of alkylate product per kg of catalyst or greater wherein the olefin conversion remains above 90%, and the Research Octane Number (RON) of the products remains above 92. Steady state means that the selectivity to C8 isomers changes by 10% or less over a time period in which the 5 kg of alkylate product is produced per kg of catalyst. For example, a change in selectivity from 80% to 72% would be a 10% change. In this method, the reaction chamber comprises a crystalline zeolite catalyst; wherein the crystalline zeolite catalyst comprises sodalite cages and supercages, a Si/Al molar ratio of 20 or less, less than 0.5 weight percent alkali metals, and rare earth elements in the range of 10 to 35 wt %. Optionally, the catalyst may comprise up to 5 wt % Pt and/or Pd; and/or Nickel. The above-mentioned first aspect is a subset of a larger aspect having the same characteristics except not requiring rare earth elements. Throughout the descriptions in this specification, percentages of Si, Al, and rare earth elements refer to the elemental composition of the zeolite crystallites (apart from the binder), which can be easily measured during catalyst synthesis, and can be determined spectroscopically or, if necessary, by physical separation of the binder and crystallite in the finished catalyst. The elemental composition of Pd, Pt, and Ni is based on the weight percent of the entire particles.

The statement that the catalyst lifetime is 2.5 or greater is not intended to mean that the catalyst age could be infinite, but that the method operates for sufficient time, without catalyst regeneration for the catalyst age to be at least 2.5. The method could be operated for sufficient time, without catalyst regeneration for the catalyst age to be 3.0. In some cases, the method can be described as having a catalyst age between 2.5 and 3.5. The method could be operated for a catalyst age greater than 3.5. A catalyst scientist would understand that the catalyst synthesis and reaction conditions described here could be optimized through routine optimization, within the limitations described in conjunction with the above-described method, to reach a natural limit to the catalyst lifetime.

In various embodiments, the method may further be characterized by one or any combination of the following options: a reaction temperature of between 45 and 90° C. (in some embodiments between 55 and 80° C., in some embodiments between 60 and 75° C.); an operating pressure of 250 to 400 psig; wherein, subsequent to the continuous operation, the catalyst is regenerated in a stream of flowing hydrogen at a temperature of at least 250° C. and a GHSV of 500 l/hr or greater; wherein the feed I/O ratio is 12 or lower, wherein the method is run continuously for 18-36 hours at an olefin hourly space velocity of 0.1 l/hr or higher without regenerating the catalyst; wherein the reaction chamber comprises a packed catalyst bed; operating the method with a recycle stream such that the ratio of the recycle stream flow rate to the feed stream flow rate is 20 or higher; wherein C8 selectivity is at least 70%; wherein the C2 to C5 olefin consists essentially of butenes; wherein the catalyst comprises 0.1 wt % to 5 wt % of Pt, Pd, Ni or combinations thereof; wherein the method is run continuously for a catalyst age of 2-3.5 without regenerating the catalyst; comprising a recycle stream such that the catalyst be I/O is greater than 300; wherein the C2 to C5 olefin consists essentially of mixed butenes; wherein the C2 to C5 olefin consists essentially of propylene; wherein the C2 to C5 olefin contains less than 2000 ppm of butadiene; wherein the C2 to C5 olefin contains less than 2 wt % isobutylene; wherein the C2 to C5 olefin contains less than 250 ppm of mercaptans; wherein the C2 to C5 olefin contains less than 300 ppm acetonitrile and less than 200 ppm propionitrile; wherein the C2 to C5 olefin contains less than 50 ppm water; wherein the method is run continuously for a catalyst age of 2.5 or a catalyst age of 3.0; and/or wherein the zeolite structure is zeolite X or zeolite Y.

In another aspect, the invention provides a method of making an alkylation catalyst, comprising: providing a crystalline zeolite structure comprising sodalite cages and supercages and having a Si/Al molar ratio of 20 or less, and a first concentration of alkali metal; contacting the zeolite with a solution comprising a rare earth metal; calcining said catalyst by heating said catalyst to a calcination temperature of at least 575° C. to produce a catalyst intermediate comprising the rare earth metal and second concentration of alkali metal that is less than the first concentration of alkali metal; contacting the catalyst intermediate with an ammonium solution, drying to remove excess solution, and then heating the catalyst to generate the hydrogen (active) form of the zeolite—the deammoniation step. In some embodiments, the calcining step comprises heating to at least 575° C., or at least 600° C., or 575° C. to 625° C., and maintaining these temperatures for at least 1 hour or at least 2 hours. The deammoniation step is typically carried out at least about 400° C. and below 500° C., in some embodiments in the range of 375 to 425° C. The deammoniation step is carried out at the stated temperature ranges for at least one hour, preferably at least two hours, or at least 4 hours, in some embodiments in the range of 1 to 10 hours, or 2 to 6 hours. The deammoniation step is conducted under the flow of an oxygen-containing, dry gas (typically dry air). The deammoniation step is conducted separately from the rare earth ion exchange and any subsequent calcination step. Preferably, the calcining step is conducted in the presence of a dry gas (preferably dry air); and desirably the entire process is conducted in the absence of steam.

The step of contacting the intermediate is separate from and subsequent to the rare earth ion exchange.

The crystalline zeolite structure starting zeolite material may comprise 5 to 20 wt %, or 5 to 17 wt %, or 10-17 wt %, or 12-17 wt % Na.

The solution comprising a rare earth metal preferably comprises $La^{3+}$, preferably an aqueous solution comprising 0.5 to 0.8 M La. Experiments were conducted with La showing the degree of exchange shown below:

Composition of LaX Catalyst with Varying Amounts of Lanthanum Concentration in Solution

| La + 3 Concentration (M) | La2O3 (wt %) | Degree of Exchange |
|---|---|---|
| 0.2 | 19.08 | 64% |
| 0.4 | 19.96 | 67% |
| 0.6 | 25.63 | 85% |
| 0.8 | 29.18 | 97% |

The "active" form (or hydrogen form as it is sometimes called) is the catalyst after a deammoniation step that can be used for alkylation.

In some embodiments, the invention includes the alkylation methods described herein but employing a β-zeolite catalyst in place of the X or Y zeolite.

Any of the methods described herein may include a step of regenerating the catalyst.

In various preferred embodiments, the method may comprise one or more of the following features: wherein the step of calcining to a temperature of at least 600° C., thereby provides a catalyst in which a portion of the alkali metal cation sites are replaced with rare earth metal cation sites and wherein the step of contacting with an ammonium solution, thereby provides a catalyst in which a portion of the alkali metal cation sites are replaced with rare earth metal cation sites, and another portion of the alkali metal cation sites are replaced with ammonium cation sites, and further wherein the deammoniation temperature does not exceed 400° C. in the presence of air, whereby at least a portion of said ammonium cation sites are replaced with H+ sites, thereby providing a catalyst in which a portion of said alkali metal cation sites have been replaced with rare earth metal cation sites and another portion of said alkali metal cation sites have been replaced with H+ sites; wherein the rare earth metal is selected from the group consisting of lanthanum, cerium, neodymium, and praseodymium, and said rare earth metal cations are selected from the group consisting of lanthanum cations, cerium cations, neodymium cations, and praseodymium cations; wherein the rare earth metal comprises lanthanum; wherein the alkali metal cation sites are sodium cation sites; wherein the catalyst has a silica to alumina ratio of from about 2 to about 35; wherein the catalyst has a silica to alumina ratio of from about 2 to about 10; wherein the solution comprising a rare earth metal comprises an aqueous $La(NO)_3$ solution; wherein the solution comprising a rare earth metal comprises an aqueous $La_2(SO_4)_3$ solution; wherein the solution comprising a rare earth metal comprises an aqueous $LaCl_3$ solution; wherein the solution comprising a rare earth metal comprises an aqueous solution of at least 0.1 M Lanthanum ions or at least 0.2 M La, or at least 0.4 M La, or at least 0.6 M La, or at least 0.8 M La, or in the range of 0.2 to 0.8 M La; wherein said catalyst is contacted with the rare earth metal solution at a temperature of from 60 to 90° C.; wherein the catalyst is contacted with the rare earth metal solution for a period of time of about 2 hours; wherein the step of calcining does not exceed 600° C.; wherein the step of calcining is conducted from 2 to 8 hours; wherein, during the calcination step, the catalyst is heated in the presence of air which has a moisture content that does not exceed 2.0 wt. % or does not exceed 0.2 wt %; wherein the ammonium solution comprises an aqueous solution of at least 0.1 M, or at least 0.2 M, or at least 0.3 M, or at least 0.5 M, or at least 1 M ammonium ions; wherein the step of contacting with an ammonium solution, which provides a catalyst in which a portion of the alkali metal cation sites are replaced with ammonium cation sites, comprises an aqueous solution of ammonium nitrate or ammonium sulfate; wherein the crystalline zeolite is selected from the group consisting of Zeolite X and Zeolite Y; preferably Zeolite X.

In another aspect, the invention provides an alkylation catalyst, comprising:
a zeolite structure comprising sodalite cages and supercages, a Si/Al molar ratio of 20 or less, less than 0.5 weight percent alkali metals, rare earth elements in the range of 10 to 35 wt % (or a molar ratio of rare earth elements to (Si and Al) in the range of 0.06 to 0.20); and
characterizable by a catalyst lifetime greater than 2.5 using a test where the solid-acid catalyst is loaded in a fixed-bed reactor such that the $d_T/d_P>10$ (diameter of tube to diameter of catalyst particles) and $L/d_P>50$ (length of catalyst bed to diameter of catalyst particles) and exposed to a) a feed stream comprising 10:1 molar ratio of isobutane:n-butenes at 60° C. and 300 psig with a recycle ratio of 50, where the ratio of system volume to catalyst volume is 7, without regeneration, and wherein the RON of the product is at least 92; or b) a feed stream comprising 100:1 molar ratio of isobutane:n-butenes at 60° C. and 300 psig without regeneration, and wherein the RON of the product is at least 92. Optionally, the catalyst may comprise from 0.1 wt % up to 5 wt % Pt and/or Pd; and/or Nickel. Since the catalyst cannot be completely distinguished from the prior art based solely on its elemental composition, the measurement described above is needed for a unique characterization of the catalyst. In various embodiments, the catalyst may be further characterized by any of the compositions or physical characteristics described herein. Preferably, particle size is in the range of 1 to 5 mm. In some preferred embodiments, $d_T/d_P>20$, or $d_T/d_P>50$ and/or $d_T/d_P>10$. Particle size can be determined by mesh size and, in preferred embodiments, catalyst particle size (including binder) is in the range of 4 mesh to 20 mesh (U.S. mesh size).

In various preferred embodiments, the catalyst may comprise one or more of the following features: a catalyst lifetime of between 2.5 and 3.5; where the Catalyst Lifetime parameter is defined as the catalyst age when the olefin conversion falls below 90% (or, in some preferred embodiments, below 95%) using a test where the solid-acid catalyst is loaded in a fixed-bed reactor such that the dT/dP>10 (diameter of tube to diameter of catalyst particles) and L/dP>50 (length of catalyst bed to diameter of catalyst particles) and exposed to a flow comprising a) a feed of 10:1 molar ratio of isobutane:n-butenes at 60° C. and 300 psig with a recycle ratio (R=volumetric flow rate of recycle stream/volumetric flow rate of feed stream) of 50, where $V_S/V_C$ is 7 (the ratio of system volume to catalyst volume), without regeneration, and wherein the RON of the product is at least 92; where the Catalyst Lifetime parameter is defined as the catalyst age when the olefin conversion falls 90% (or, in some preferred embodiments, below 95%) using a test where the solid-acid catalyst is loaded in a fixed-bed reactor such that the dT/dP>10 (diameter of tube to diameter of catalyst particles) and L/dP>50 (length of catalyst bed to diameter of catalyst particles) and exposed to a flow comprising a feed stream comprising 100:1 molar ratio of isobutane:n-butenes at 60° C. and 300 psig without regeneration, and wherein the RON of the product is at least 92. In various embodiments, the catalyst may have any of the other characteristics described anywhere in this specification.

In another aspect, the invention provides a method of making an alkylation catalyst, comprising: providing a (a)

β-zeolite or (b) a crystalline zeolite structure comprising sodalite cages and supercages; and having a Si/Al molar ratio of 20 or less (preferably 15 or less or 10 or less, or in the range of 2.5 to 20 or 15 or 10 or in the range of 5 to 20 or 15 or 10), and heating to a temperature in the range of 375 to 500° C., preferably 375 to 425° C., or 400 to 450° C., in the presence of an oxygen-containing gas (typically air) to convert the catalyst to the active form. In some preferred embodiments, the method comprises one or more of the features: the step of heating to a temperature is conducted for at least 1 hour; further comprising a step of treating the β-zeolite or crystalline zeolite structure with a solution comprising Pd, Pt, or Ni, or a combination thereof; wherein the alkylation catalyst comprises the crystalline zeolite structure, the zeolite structure comprising an alkali metal, and wherein, prior to the step of heating, contacting the zeolite structure comprising an alkali metal with an ammonium solution and then drying to remove excess solution; wherein the active form is disposed in a fixed bed reactor and passing isobutane and C2 to C5 olefins.

In a further aspect, the invention provides a method of alkylating isobutane, comprising: passing a feed mixture consisting of excess isobutane and C2 to C5 olefins into a reaction chamber; wherein the reaction chamber comprises a crystalline β-zeolite catalyst;
wherein the crystalline β-zeolite catalyst comprises a Si/Al molar ratio of 20 or less, less than 0.5 weight percent alkali metals; and up to 5 wt % of Pt, Pd and or Nickel, wherein, at steady state, at least 90% of the butenes (or at least 90% of the C2 to C5 olefins) are converted to products and wherein the Research Octane Number (RON) remains above 92; and conducting the process for a catalyst age of 2.5 or greater over the same catalyst; and wherein steady state means that the selectivity to C8 isomers changes by 10% or less over the entire period that the catalyst age is determined.

In another aspect, the invention provides an alkylation reaction system, comprising: a reactor comprising a multi-stage reaction chamber comprising a fixed bed of zeolite catalyst;
the reaction chamber comprising 4 to 8 stages each comprising an inlet, wherein olefin flow is distributed through the inlets into the 4 to 8 stages; a product stream comprising alkylate; and
a recycle pump that recycles the product stream at a recycle ratio of 6 to 10. In this system, both the solid and fluid elements are considered components of the system. The term "stages" may alternatively be described as zones. In a preferred embodiment, the reaction chamber comprises 4-6 stages wherein olefin flow is distributed to the 4-6 stages.

The invention also includes a β-zeolite catalyst or X or Y zeolite catalyst, comprising: a Si/Al molar ratio of 20 or less, less than 0.5 weight percent alkali metals, and, optionally up to 5 wt % Pt and/or Pd; and/or Nickel; and characterizable by a Catalyst Lifetime of 2 or greater as described above. The catalysts may include any of the features discussed in this specification.

The invention also includes systems that can be defined as reactor apparatus plus the reactants and/or reactant products and/or conditions within the reactor apparatus.

Glossary

Beta-zeolite (β-zeolite)—Is a known form of zeolite that is a highly intergrown hybrid of two distinct, but closely related structures that both have fully three-dimensional pore systems with 12-rings as the minimum constricting apertures. See Newsam et al., "Structural Characterization of Zeolite Beta," Proc. of Royal Soc., A (1988)

Calcination Temperature—The term "calcination temperature" refers to the maximum temperature utilized as an intermediate step in the catalyst synthesis procedure intended to remove the hydration sphere from lanthanum ions and allow solid-state exchange between lanthanum and sodium cations in the sodalite and supercages.

Deammoniation Temperature—The temperature at which the catalyst is converted from an ammonium form to its active (H+) form is referred to here as the "deammoniation temperature." This step first converts the ammonium form of the active sites to Bronsted acid sites (H+), further dehydroxylation may convert active sites to Lewis acid sites.

Regeneration Temperature—The solid acid catalyst may be regenerated under flowing hydrogen gas at elevated temperatures in order to hydrocrack heavier hydrocarbons and remove them from the zeolitic structure. The maximum temperature used in this step is referred to as the "regeneration temperature."

Conversion—The term "conversion of a reactant" refers to the reactant mole or mass change between a material flowing into a reactor and a material flowing out of the reactor divided by the moles or mass of reactant in the material flowing into the reactor. For example, if 100 grams of olefin are fed to a reactor and 10 grams of olefin exit the reactor, the conversion is [(100–10)/100]=90% conversion of olefin.

Olefins—As used herein, the terms "olefin" or "olefin compound" (a.k.a. "alkenes") are given their ordinary meaning in the art, and are used to refer to any unsaturated hydrocarbon containing one or more pairs of carbon atoms linked by a double bond. In this invention, $C_2$-$C_5$ olefins refers to ethylene, propylene, n-butylenes, isobutylene, and the various isomers of pentene. The phrase "$C_2$-$C_5$ olefins" has the standard meaning encompassing any combination of olefins in the C2 to C5 range, with no minimum requirement for any of the C2 to C5 compounds. In some preferred embodiments, the C2 to C5 olefins contain at least 50 wt % C4 olefins as a percent of all olefins.

Olefin Hourly Space Velocity (OHSV)—"Olefin Hourly Space Velocity" is defined as the mass flow rate of olefin fed to the reactor per hour divided by the mass of catalyst in the reactor.

Recycle Ratio (R)—The "recycle ratio" is defined as the volumetric flow rate of the recycle stream divided by the volumetric flow rate of the feed stream.

Feed I/O Ratio—In alkylation experiments the concentration of olefin in the feed is often expressed as a ratio of isobutane to olefinic species by mole in the reactor feed ("Feed I/O Ratio"). A Feed I/O Ratio ($I/O_{feed}$) of 100 is equivalent to ~1% olefin in isobutane—$I/O_{feed}$ of 10 is equivalent to ~9.1% olefin in isobutane.

Catalyst Bed I/O Ratio—In the reactor schemes discussed in this patent, the solid acid catalyst is exposed to isobutane to olefin ratios much higher than those in the reactor feed. This is achieved by both spreading the feed over a number of evenly distributed inlets along the catalyst bed (N=the number of inlets) and/or utilizing a recycle stream. The "catalyst bed I/O ratio" is calculated as: $I/O_{bed}=N*I/O_{feed}+R(I/O_{feed}-1))$.

System Volume—The total volume of the reactor and any tubing for feed delivery, recycle lines, sample extraction from the exit of the feed pumps to the back pressure regulator of the reactor system.

Catalyst volume: The bulk volume where solid catalyst (including void spaces between catalyst particles) is present at reaction conditions is defined as the "catalyst volume." In the preferred case of a fixed catalyst bed, the bulk volume includes catalyst particles and voids between particles. For example, in one preferred embodiment, a fixed catalyst has 0.62 catalyst particle fraction and 0.38 void fraction. In some embodiments of the invention, the catalyst bed comprises between 0.38 to 0.85 void fraction.

Catalyst Age—"Catalyst age" is the mass of olefin fed to the reactor divided by the mass of catalyst.

Catalyst Lifetime—The catalyst age at which the olefin conversion falls below 90% is defined as the "catalyst lifetime."

Pore size—Pore size relates to the size of a molecule or atom that can penetrate into the pores of a material. As used herein, the term "pore size" for zeolites and similar catalyst compositions refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998.

Residence Time—Residence time is the time a substance is in the reaction vessel. It can be defined as the volume of the reactor divided by the flow rate (by volume per second) of gases into the reactor.

Selectivity—The term "selectivity" refers to the amount of production of a particular product (or products) as a percent of all products resulting from a reaction. For example, if 100 grams of products are produced in a reaction and 80 grams of octane are found in these products, the selectivity to octane amongst all products is 80/100=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis.

Yield—The term "yield" is used herein to refer to the amount of a product flowing out of a reactor divided by the amount of reactant flowing into the reactor, usually expressed as a percentage or fraction. Mass yield is the mass of a particular product divided by the weight of feed used to prepare that product.

When unspecified, "%" refers to mass % which is synonymous with weight %. Ideal gas behavior is assumed so that mole % is the same as volume % in the gas phase.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

DETAILED DESCRIPTION OF THE INVENTION

Figure 1:
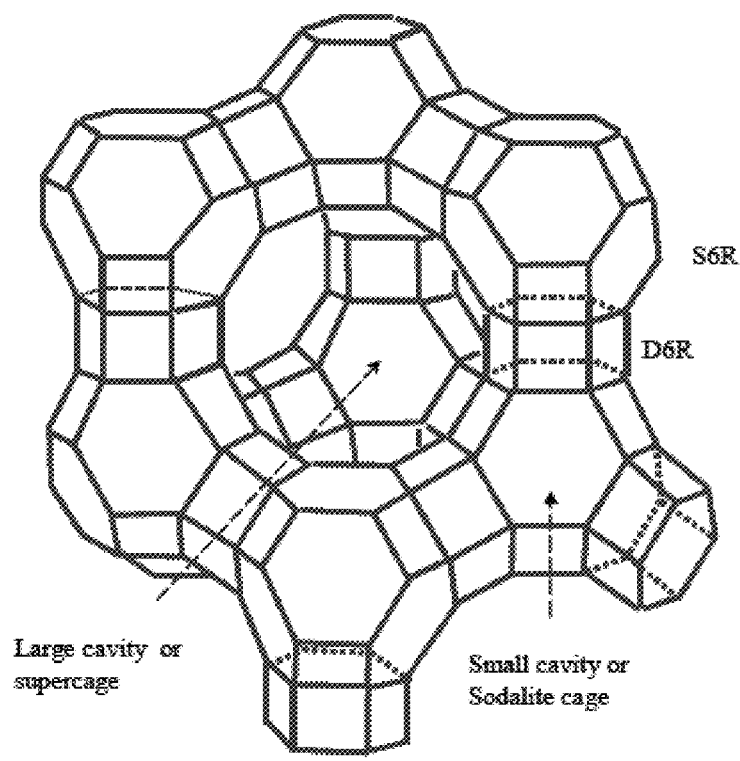
FIG. 1: Faujasite Structure of zeolite X and Y

The invention relies on a solid acid, crystalline zeolite structure that has both supercages and sodalite cages. These structures are well known and are shown in FIG. 1. It is believed that Bronsted acid sites in the supercages are important in catalyzing the alkylation reaction. The Faujasite structure with supercages and sodalite cages is known in Zeolite X and zeolite Y. Commercial zeolites are typically mixed with binders. The purity of zeolites can be measured by oxygen adsorption as described in Experimental Methods in Catalytic Research, vol. 2, Anderson and Dawson eds. (1976). Thus, although the invention can operate with pure crystalline zeolite, it typically operates with crystalline zeolite mixed with binder or other materials. Relatively high levels of aluminum are desirable; thus it is desirable to use zeolites with a Si/Al molar ratio of 20 or less, preferably 15 or less, in some embodiments in the range of 1 to 12, in some embodiments in the range of 2 to 10. We have found excellent results based on Zeolite X and acceptable performance with zeolite Y; nonetheless, based on the similarity of the pore structure, it is believed that zeolite Y should also function as a suitable starting material for the catalyst of the invention. The pore size of the sodalite cage structure does not exceed about 8 Angstroms, and the supercage structure has pores in which the pore size is at least about 10 Angstroms. In some preferred embodiments, the Si/Al molar ratio of zeolite X is in the range of 1 to 2; the Si/Al molar ratio of zeolite Y is in the range of 2 to 5; the Si/Al molar ratio of beta zeolite is in the range of 8 to 13.

In a method of making a catalyst according to the present invention, a material containing a crystalline zeolite structure comprising sodalite cages and supercages and having a Si/Al molar ratio of 20 or less is treated with a solution containing a rare earth metal. The crystalline zeolite structure contains an alkali metal, typically sodium or potassium, most typically, sodium. The amount of alkali metal in the starting material is typically greater than 1 wt %, in some preferred embodiments greater than 3 wt %, in some embodiments between 5 and 20 wt %. The solution containing a rare earth metal is typically an aqueous solution. Preferred rare earth metals comprise lanthanum, cerium, neodymium, and praseodymium, and mixtures thereof; most preferably comprise lanthanum (La), and in some preferred embodiments the rare earth metal is at least 90% La or at least 95% La (by weight relative to total weight of all rare earth metals in solution). Preferably, the zeolite is treated with the rare earth solution at elevated temperature, preferably from 60 to 95° C., more preferably 70 to 90° C.; typically with a nitrate or sulfate salt solution. The solution containing a rare earth metal preferably has a concentration in the range of 0.1 M to 1.0 M, in some embodiments in the range of 0.4 to 0.8 M. Multiple treatments, for example, 3 treatments are preferred. Each treatment is preferably conducted for at least one hour at the elevated temperature, in some embodiments between 1 and 4 hours.

If there is excess solution containing rare earth metal, it can be removed by decanting or filtering. Optionally, after decanting or filtering, the treated zeolite can be dried at temperatures up to 100° C. The resulting material is believed to have rare earth metal located in the supercages, but not yet exchanged with the alkali metal in the sodalite cages.

To effectuate exchange of alkali ions in the sodalite cages with the rare earth ions located in the supercages, the catalyst is calcined at a temperature of at least 575° C. Although it was reported that the amount of $La^{+3}$ in the sodalite cages becomes constant at temperatures above 300° C. (Monsalve, Thesis "Active Acid Sites in Zeolite Catalyzed Iso-butane/cis-2-butene Alkylation" Chap. 3, p 4), we surprisingly found significantly improved results from calcining at a much higher temperature. Preferably, the calcining step is carried out at a temperature of 575 to 650° C. In some preferred embodiments, the zeolite is held at a temperature between about 90 and 110° C. for at least 10 minutes, preferably at least 50 minutes. The zeolite can be heated at any suitable temperature ramping rate; for example between 1° C./min to 10° C./min. It may be preferred to hold the temperature at an intermediate value, such as between 200 and 300° C. for 30 min or more. Preferably, the zeolite is maintained at a temperature of at least 575° C., preferably between 575 and 650° C., in some embodiments between 600 and 625° C., or from 575 to 600° C., for at least 50 minutes, preferably for at least about 100 minutes; in some embodiments for between 50 and 500 minutes, in some embodiments between 50 and 240 minutes. Preferably, the entire calcination process, including temperature ramping times, is completed within 1 day, or completed within 2 days. The calcination step is preferably carried out at a relatively low humidity, for example, in dry flowing air containing less than 1 mass % water, in some embodiments less than about 50 ppm water. We believe that the calcination step causes some and, preferably essentially all, of the alkali metal ions (usually $Na^+$) in the sodalite cages to be replaced with the rare earth ions (preferably La+3) from the sodalite cages.

After calcination, the calcined zeolite is cooled and treated with an ammonium solution. The solution preferably has an ammonia concentration in the range of 0.1 M to 1.0 M, in some embodiments in the range of 0.2 to 0.5 M. This can be repeated several times; for example, from 2 to 5 times. One preferred set of conditions for the ammonium treatment is a temperature of from 50 to 100° C. for 10 minutes to 4 hours or more; more preferably from 30 minutes to two hours. In some embodiments of the invention, there is no rare earth exchange step and the zeolite (typically zeolite Y; containing Na cations) can be treated by the ammoniation process described herein.

Any excess solution can be removed by decanting or filtration. The ammonium-exchanged zeolite can be heated to drive off excess water, for example to 100° C. or 200° C.

Prior to use as a catalyst, the zeolite is converted from its ammonium form to the hydrogen form by heating, preferably in an atmosphere having very little water; for example, 1 mass % or less, or 0.2 mass %, or 2 ppm or less of water. This deammoniation temperature is preferably in the range of 300 to 400° C., more preferably 350 to 400° C.

Although the scope of the present invention is not to be limited to any theoretical reasoning, it is believed that the deammoniation step converts the ammonium cation sites to Bronsted acid sites, especially in the supercages, while the rare earth elements remain in the sodalite cages. Because the acid, or H+, sites are located in the larger diameter supercage structure of the catalyst, pore mouth plugging is significantly reduced, allowing the catalyst to remain active for increased periods of time, while the rare earth metal cation sites, such as, for example, $La^{+3}$ sites, provide enhanced stability to the sodalite structure. We believe that at least 80% of the cationic sites in the sodalite portion are rare earth metal cation sites, and at least 80% of the cationic sites in the supercage portion are H+ sites.

We have found that careful control of the deammoniation conditions for the zeolite catalyst lead to improvements in catalyst performance, when converting the ammonium form of the zeolite to the active or acid form. When the ammonium form of a zeolite is heated, the initial step is the evolution of physically adsorbed water, which causes a first endotherm at about 150° C.; this step is completed at 200° C. Ammonia then is evolved which gives rise to a second endotherm at 300° C.; this step is completed at about 400° C. Raising the temperature above 400° C. results in evolution of water from the condensation of the hydroxyl groups. This dehydroxylation step results in a) a significant decrease in the number of active catalytic acid sites and b) conversion of the preferred Bronsted acid sites to the Lewis acid sites which increases the rate of catalyst deactivation.

The invention also relates to a reactor suitable for paraffin alkylation using solid acid catalysts. Paraffin alkylation is a fast reaction, which benefits from low olefin concentrations (typically the reactor I/O ratio>300) in the reactor to suppress the polymerization reaction. In conventional liquid-acid based reactors, high speed mechanical agitators are used to disperse the hydrocarbon feed into the acidic medium. Specially designed jets are used to introduce the olefin feed as small droplets to avoid high localized olefin concentration. A departure from perfect mixing conditions results in significant deterioration of product octane quality and formation of Acid Soluble Oils via olefin polymerization reaction which leads to higher acid consumption. The only way to achieve the same level of mixing with solid-catalysts, is to use a slurry system. However, slurry systems are difficult to handle and equipment needed to pump slurries around are very expensive.

Figure 2:
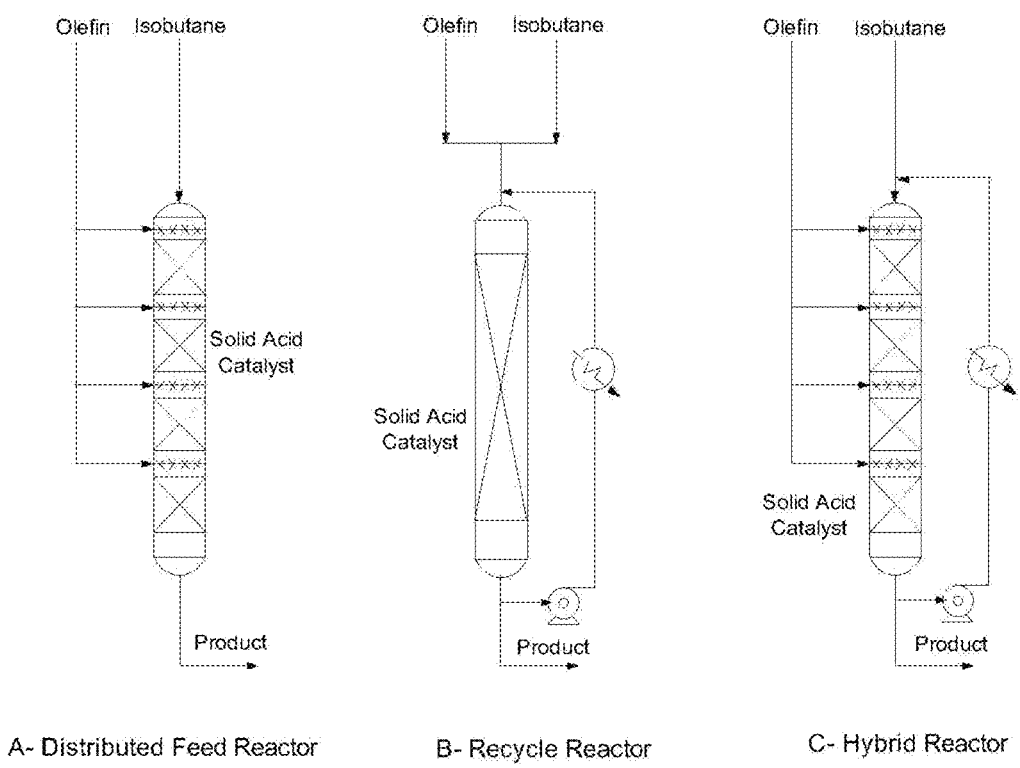
FIG. 2: Fixed-Bed Reactor configurations suitable for solid-acid alkylation

Fixed-bed reactors are easier to design, scale-up and maintain and, therefore, preferred embodiments utilize a fixed bed reactor. One way of achieving a low olefin concentration in the bulk liquid is obtained by staging the olefin feed over the catalyst bed. This approach is often used in designing reactors for aromatic alkylation reactions for the production of ethylbenzene or cumene. Typically 4-6 stages (FIG. 2A) are used in designing such reactors. In paraffin alkylation reactions, the feed mixture of iso-butane to olefins (I/O) range from 10-15 molar and a typical catalyst bed I/O target is 300-500. This implies that the olefin must be distributed in 30-50-stages to meet this recommended dilution in olefin concentration which is difficult to achieve in commercial scale reactors. Another way of achieving this level of olefin dilution without resorting to staging the feed is by introducing a recycle stream of the reactor effluent (FIG. 2B). By using a recycle ratio of 30-50, a feed with an I/O ratio of 10-15 would produce a catalyst bed I/O of 300-500. However, the large volumetric flow through the catalyst bed would generate a proportionally large pressure-drop greatly increasing the duty (hence power consumption) on the recycle pump. A novel way of designing a fixed-bed reactor for solid acid catalyzed reactions is to combine the two concepts into a hybrid reactor (FIG. 2C) where the olefin feed is staged over 4-6 zones and the recycle pump recycles the product stream at a modest recycle ratio of 6-10. This allows a catalyst bed I/O of 300-500 without resorting to a large number of feed stages or a very high recycle ratio. An added benefit of this design is the ability to remove the heat of reaction externally. The invention includes methods using the reactors described herein and includes systems (apparatus plus fluids and, optionally, conditions within the apparatus) that includes the reactors described herein.

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

EXAMPLES

Example 1—Catalyst A

The starting material was a commercial zeolite X having a $SiO_2/Al_2O_3$ molar ratio of 2.8 (Si/Al of 1.4) and a sodium content of 15% by weight. 5 grams of the zeolite was crushed and sieved to 0.5-1.4 mm particles. They were suspended in 50 mL of deionized water and stirred for 15 minutes after which the water was decanted. This washing procedure was repeated a second time.

A lanthanum ion exchange was performed immediately following the initial water wash. The zeolite was suspended in 50 mL of a 0.8 M lanthanum nitrate solution and heated to 80° C. while stirring for 2 hours. The lanthanum solution was decanted and replaced with a fresh solution. This lanthanum exchange was performed three times followed by 2 water washes of 75 mL each. The zeolite was then left to dry at room temperature.

Following the lanthanum exchange, the zeolite was calcined in a muffle furnace. The temperature program for calcination was 1.5° C./min ramp to 100° C. where it was held for 1 hour, 2.0° C./min ramp to 230° C. and hold for 2 hours, 10° C./min ramp to the final calcination temperature of 400° C. for 4 hours.

The lanthanum exchanged zeolite was suspended in a 0.5 M ammonium nitrate solution and heated to 80° C. with stirring for 2 hours. The ammonium solution was decanted and replaced with fresh solution. This ion exchange was performed 3 times followed by 2 water washes of 75 mL each. The zeolite was then left to dry at room temperature. The zeolite was deammoniated in dry air (<2 ppm) using the following temperature program: 100° C. (0.5 hours), 120° C. (1 hour), 230° C. (2 hours), 400° C. (4 hours). 400° C. is the deammoniation temperature required to convert the catalyst from the ammonium form to the active proton form. The lower temperatures are necessary to completely dry the catalyst.

Example 2—Catalyst B

The catalyst was prepared as in Example 1 with the only difference being the final calcination temperature. In this example the final calcination temperature following lanthanum exchange was 450° C.

Example 3—Catalyst C

The catalyst was prepared as in Example 1 with the only difference being the final calcination temperature. In this example the final calcination temperature following lanthanum exchange was 550° C.

Example 4—Catalyst D

The catalyst was prepared as in Example 1 with the only difference being the final calcination temperature. In this example the final calcination temperature following lanthanum exchange was 600° C.

Example 5—Catalyst E

The catalyst was prepared as in Example 1. However, the starting material used was a Y zeolite in this example. The commercial Y zeolite had a $SiO_2/Al_2O_3$ molar ratio of 5.0 and a sodium content of 14% by weight. Since the Y zeolite is in powder form it must be filtered rather than decanted in each solution exchange. Additionally, it is pelletized following ammonium exchange and drying then crushed and sieved to 0.5-1.4 mm catalyst particles.

Example 6—Catalyst F

The catalyst was prepared as in Example 5 with the only difference being that no Lanthanum exchange and subsequent calcination was performed. Following the initial water wash, the Y zeolite undergoes an ammonium exchange and deammoniation. In this example the deammoniation temperature was 400° C.

Example 7—Catalyst G

The catalyst was prepared as in Example 5 with the only difference being that no Lanthanum exchange and subsequent calcination was performed. Following the initial water wash, the Y zeolite undergoes an ammonium exchange and deammoniation. In this example the deammoniation temperature was 550° C.

Example 8—Catalyst H

The catalyst was prepared as in Example 3 with the only difference being water content of the air used for activation following ammonium exchange. In this example, the water content was 1.2% by volume.

Example 9—Catalyst I

The catalyst was prepared as in Example 3 with the only difference being the deammoniation temperature used following ammonium exchange. In this example the deammoniation temperature was 300° C.

Example 10—Catalyst J

The catalyst was prepared as in Example 3 with the only difference being the deammoniation temperature used following ammonium exchange. In this example the activation temperature was 350° C.

Example 11—Catalyst K

The catalyst was prepared as in Example 3 with the only difference being the deammoniation temperature used following ammonium exchange. In this example the deammoniation temperature was 450° C.

Example 12—Catalyst L

The catalyst was prepared as in Example 3 with the only difference being the deammoniation temperature used following ammonium exchange. In this example the deammoniation temperature was 500° C.

Example 13—Catalyst M

The catalyst was prepared as in Example 1. However, the starting material used was a β zeolite in this example. The commercial β zeolite had a $SiO_2/Al_2O_3$ molar ratio of 16. The β zeolite does not undergo a lanthanum exchange and the subsequent calcination. Following an initial water wash, it is immediately exchanged with ammonium 3 times. It is then deammoniated in dry air with a final temperature of 400° C.

Example 14—Catalyst N

The catalyst was prepared as in Example 13 with the only difference being the deammoniation temperature used following ammonium exchange. In this example the deammoniation temperature was 450° C.

Example 15—Catalyst O

The catalyst was prepared as in Example 13 with the only difference being the deammoniation temperature used following ammonium exchange. In this example, the deammoniation temperature was 500° C.

Example 16—Catalyst P

The catalyst was prepared as in Example 13 with the only difference being the deammoniation temperature used following ammonium exchange. In this example the deammoniation temperature was 550° C.

Example 17—Catalyst Q

The catalyst was prepared as in Example 13 with the only difference being the starting β-zeolite had a $SiO_2/Al_2O_3$ molar ratio of 25.

Example 18—Catalyst R

The catalyst was prepared as in Example 13 with the only difference being the starting β-zeolite had a $SiO_2/Al_2O_3$ molar ratio of 75.

Example 19—Catalyst S

The catalyst was prepared as in Example 17 with the only difference being the deammoniation temperature used following ammonium exchange. In this example the deammoniation temperature was 550° C.

Example 20—Catalyst T

The catalyst was prepared as in Example 18 with the only difference being the deammoniation temperature used following ammonium exchange. In this example the deammoniation temperature was 550° C.

Example 21—Catalyst U

The catalyst was prepared as in Example 4 with the only difference being the lanthanum ion exchange was performed using a 0.3 M lanthanum nitrate solution.

Example 22—Catalyst V

The catalyst was prepared as in Example 4 with the only difference being the lanthanum ion exchange was performed using a 0.5 M lanthanum nitrate solution.

Example 23—Catalyst W

The catalyst was prepared as in Example 4 with the only difference being the lanthanum ion exchange was performed using a 0.6 M lanthanum nitrate solution.

Example 24—Catalyst X

The catalyst was prepared as in Example 4 with the only difference being the lanthanum ion exchange was performed using a 0.8 M lanthanum nitrate solution.

Example 25—Catalyst Y

The catalyst was prepared as in Example 4 with the only difference being the lanthanum ion exchange was performed using a 1.0 M lanthanum nitrate solution.

Example 26—Catalyst Z

The catalyst was prepared as in Example 21. The catalyst was impregnated with Tetraamine Platinum Chloride to give 0.1 wt % Pt loading on the catalyst.

Example 27—Catalyst AA

The catalyst was prepared as in Example 24. The catalyst was impregnated with Nickel Nitrate to give 0.25 wt % Nickel loading on the catalyst.

Alkylation activity experiments were performed using an isothermal packed bed reactor setup. Heating is controlled using an Omega temperature control unit and a ceramic heating element. Feeds are sent through a preheater of ~75 cm length prior to entering the reactor.

Figure 3:
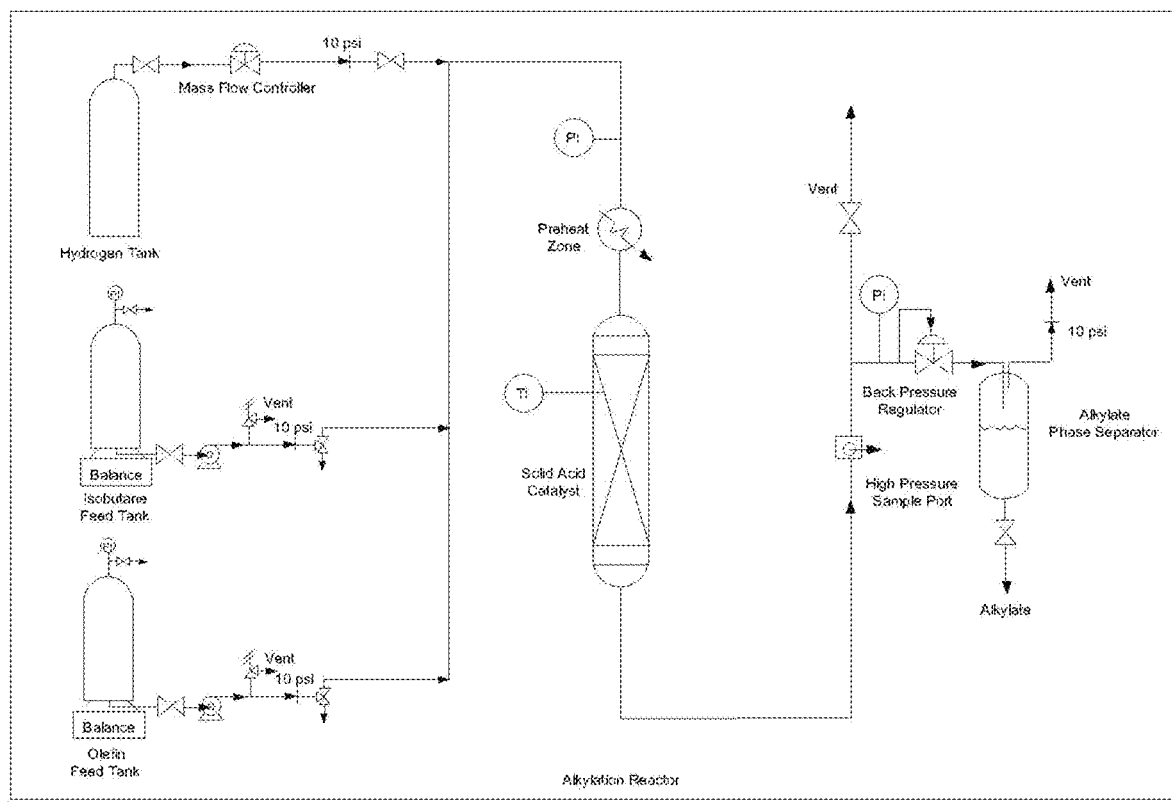
FIG. 3: Fixed-bed micro-reactor for catalyst tests

The catalyst of interest (1 g) is first loaded into a reactor shown in FIG. 3 (7.9 mm diameter), a center thermocouple (K-type) is inserted and positioned such that the tip of the thermocouple (3.1 mm diameter) is at the bottom of the catalyst bed. 1 mm glass beads are used to fill any void space in the reactor. The catalyst is deammoniated in dry air (GHSV=1000 hr$^{-1}$) at atmospheric pressure using the following temperature program: 100° C. (0.5 hour), 120° C. (1 hour), 230° C. (2 hours), 400° C. (4 hours) (these values are for Example 1). Following deammoniation the reactor is allowed to cool to reaction temperature (75° C.), then purged with dry nitrogen (GHSV=1000 hr$^{-1}$) for 0.5 hours. The reactor is pressurized (300 psig) with pure isobutane to begin the experiment.

The reaction feed is contained in helium-purged Hoke cylinders. Isobutane and 1-butene (source for both is AGL Welding Supply Co, Ltd) are analyzed for any impurities using a HP5890 GC equipped with a Petrocol DH column. All feed and product analysis uses this GC system with the following program: 60° C. (16 min), ramp at 15° C./min to 245° C. and soak (20 min).

The experiment is run using an olefin hourly space velocity equal to 0.5 hr$^{-1}$ and a feed I/O ratio of ~100. This equates to 40 g/hr feed rate for isobutane and 0.4 g/hr for 1-butene. The flow rates are controlled by Eldex ReciPro Model A pumps. Product samples are extracted using a high pressure sampling port and syringe (Vici Precision Sampling) and immediately injected into the HP5890 GC for analysis.

Figure 4:
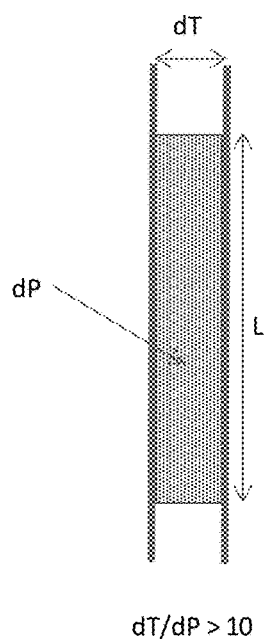
FIG. 4: Detailed reactor dimensions for catalyst tests. L is the length of the catalyst bed, dT is the tube diameter and dP is the catalyst particle diameter.

Regeneration may be performed using hydrogen gas (1000 hr$^{-1}$ GHSV) at a regeneration temperature of 250° C. for 2 hours. Process and detailed reactor schematics are shown in FIGS. 3 and 4.

Application Example 1

The lanthanum exchanged X zeolites were prepared with different calcination temperatures as in Examples 1-4 (Catalyst A-D). 1 gram of each catalyst was loaded into a reactor shown in FIG. 3. The reactor was purged with nitrogen at a temperature of 75° C. It is then pressurized with isobutane to 300 psig. The reaction feed mixture, I/O Ratio of 100, was fed to the reactor with an OHSV of 0.5 hr$^{-1}$. Product samples were withdrawn periodically from a high pressure sample port and analyzed using a gas chromatograph equipped with a Petrocol DH 100 m column.

Figure 5:
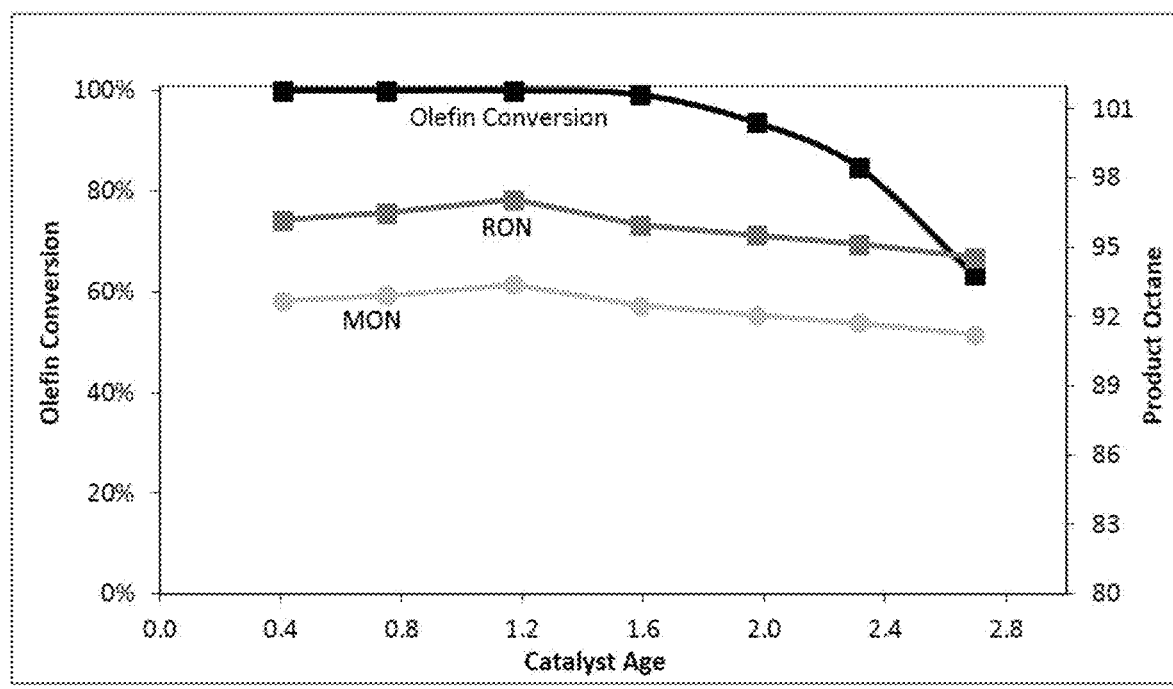
FIG. 5: Representative solid-acid alkylation experimental results for Catalyst A.

FIG. 5 shows representative data using catalyst A from Example 1. Research Octane Number (RON) and Motor Octane Number (MON) are calculated for the alkylate from product analysis.

Figure 6:
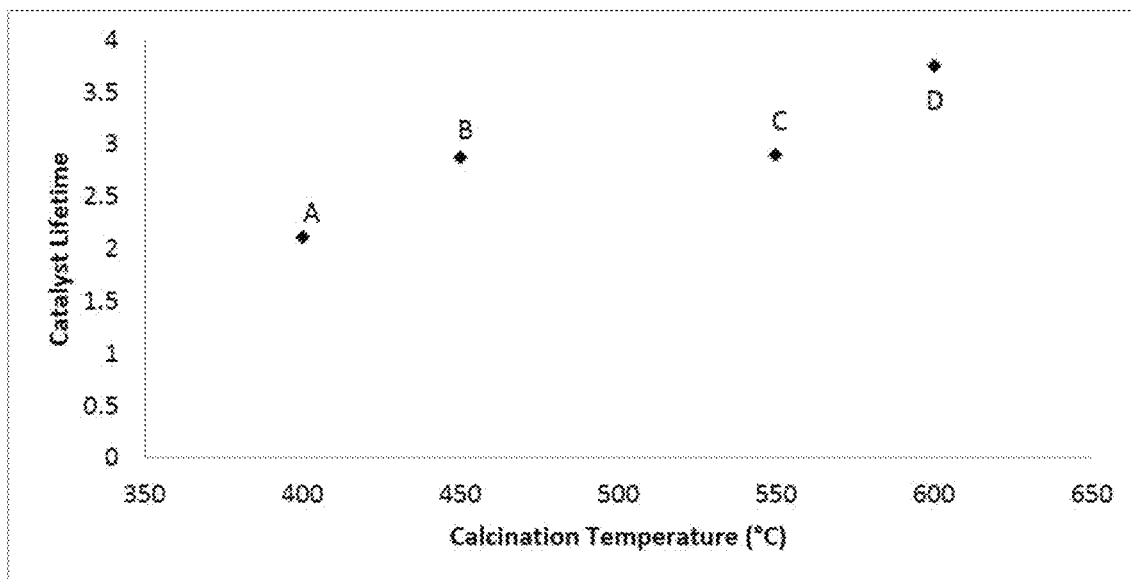
FIG. 6: Catalyst lifetime for lanthanum exchanged X zeolite calcined at different temperatures (catalysts A-D).

FIG. 6 shows catalyst lifetime as a function of calcination temperature. The zeolite calcined at 600° C. (Catalyst D) possessed a lifetime of 3.75.

As can be seen from FIG. 6, catalyst lifetime plateaus between 450 and 550° C.—an observation which matches the conventional understanding that the zeolite catalyst be calcined at a temperature of 450° C. or less. Surprisingly, however, we discovered that heating to 575° C. or higher, more preferably 600° C. resulted in a substantial improvement in catalyst lifetime, and preferably less than 650° C. to avoid degradation of the zeolite structure.

Application Example 2

The Y zeolites were prepared with and without lanthanum exchange steps followed by calcination as in Examples 5 and 7 (Catalysts E-G). The experimental conditions are identical to those of Application Example 1.

Figure 7:
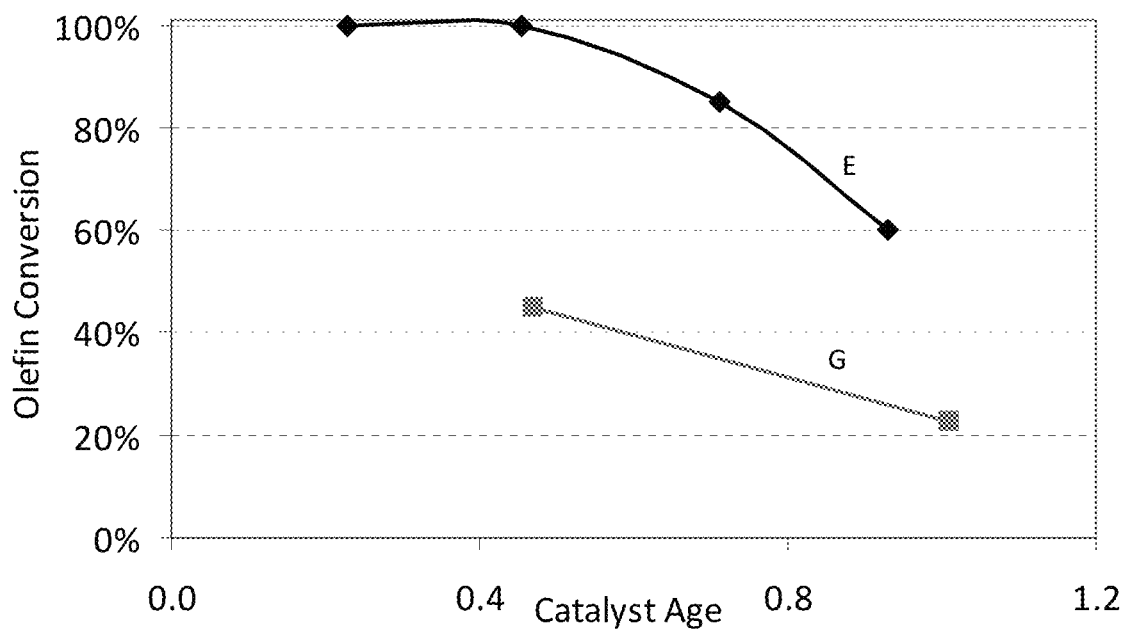
FIG. 7: Catalyst lifetime for Y zeolite with (E, top line) and without (G, bottom line) a lanthanum exchange and subsequent calcination.

FIG. 7 shows butene conversion as a function of catalyst age for the Y zeolites. As shown, the catalyst age of the H form of zeolite Y is substantially increased by lanthanum exchange followed by calcination.

Application Example 3

The catalysts used were catalyst D (<2 ppm) and catalyst H (Example 8, 1.2% by volume) at different water contents in the air during deammoniation. The experiment is identical to Application Example 1.

Figure 8:
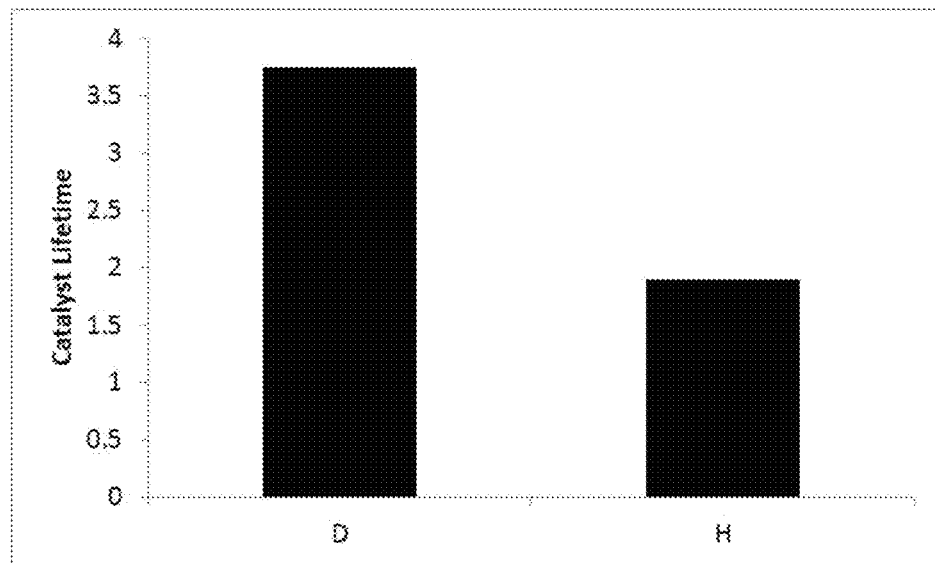
FIG. 8: Catalyst lifetime for lanthanum exchanged X zeolite deammoniated with different moisture levels of <2 ppm (catalyst D) and 1.2% by vol. (catalyst H).

FIG. 8 shows catalyst lifetime for both the water concentrations used during deammoniation. Moisture in the oxidizing gas (typically air) during deammoniation should be avoided. Therefore, the atmosphere (or, more typically, the gas that flows over the zeolite as measured prior to contacting the zeolite) during deammoniation preferably comprises 0.2 vol % or less, more preferably 10 ppm or less, more preferably 5 ppm or less, and still more preferably 2 ppm or less water.

Application Example 4

Figure 9:
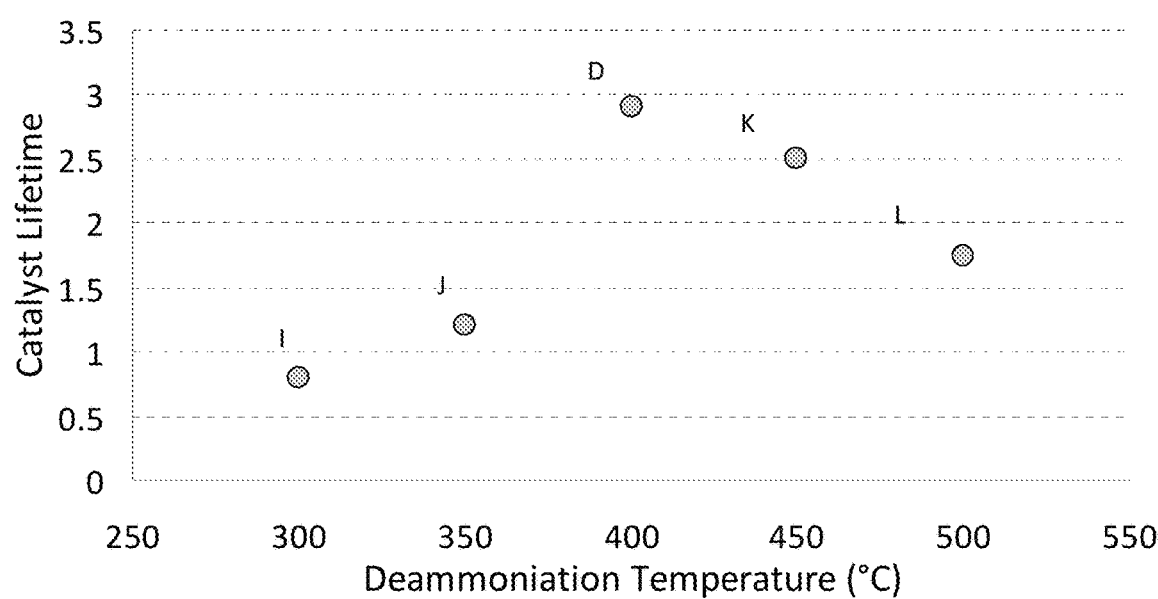
FIG. 9: Catalyst lifetime for lanthanum exchanged X zeolite deammoniated at different temperatures (catalysts D and I-L).

The catalysts used were from examples 4 (catalyst D) and 9-12 (catalysts I-L). They were deammoniated at different temperatures under dry conditions (<2 ppm). FIG. 9 compares lifetime for the catalysts deammoniated at different temperatures. There is a maximum catalyst lifetime of 2.9 at 400° C. deammoniation temperature. The deammoniation temperature was maintained at 400° C. for 4 hours.

The superior catalyst lifetime results for deammoniation in the range of about 400 to 450° C. was especially surprising since the guidelines from Linde Molecular Sieves—"Catalyst Bulletin, Ion-Exchange and Metal Loading Procedures" state that to decationize $NH_4^+$ exchanged molecular sieve should be conducted in dry air at 550° C. for 3-4 hours.

Application Example 5

Figure 10:
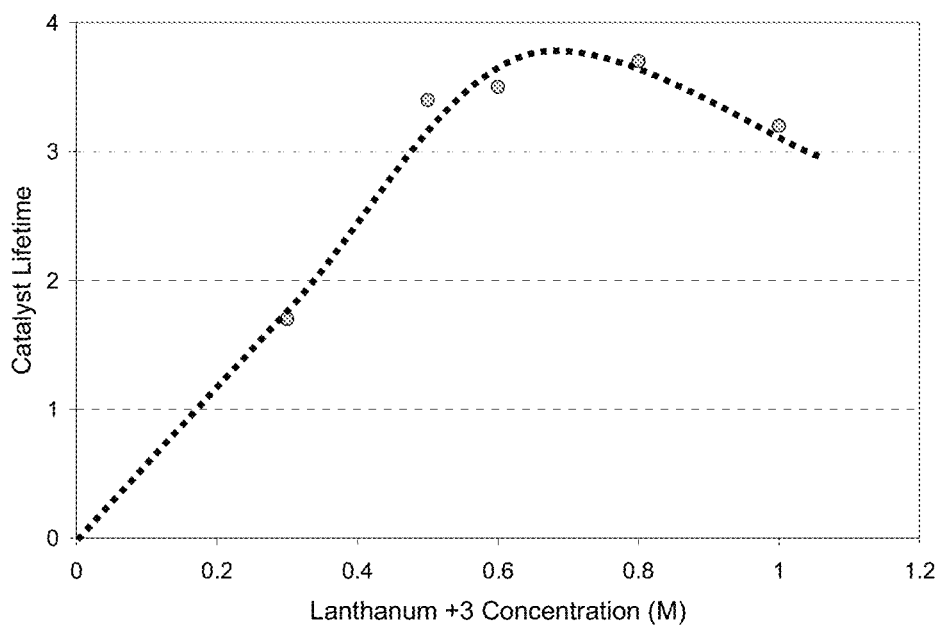
FIG. 10: Catalyst lifetime for lanthanum exchanged X zeolite at varying La+3 concentrations.

The catalysts used were from examples 18-22 (catalysts R—V). They were deammoniated at 400° C. under dry conditions (<2 ppm). FIG. 10 compares lifetime for the catalysts ion-exchanged with varying concentrations of Lanthanum Nitrate solutions. There is a maximum catalyst lifetime of 3.7 at 0.8 M Lanthanum Nitrate concentration. FIG. 10 shows that catalyst lifetime reaches a maximum, in a single exchange step, where La concentration is in the range of about 0.5 to 0.9 M, preferably 0.6 to 0.8 M; La concentrations above this range lowers pH and thus causes structural collapse.

Application Example 6

The β zeolites were prepared with different deammoniation temperatures as in Examples 13-16 (Catalyst M-P) and loaded into a fixed-bed reactor. In this experiment the reaction was run in recycle mode. The reaction feed mixture, I/O Ratio of 15, was fed to the reactor at a rate of 10 g/hr. The recycle stream flow rate was 40 g/hr. The combined feed rate to the reactor was 50 g/hr with an OHSV of 0.2 $hr^{-1}$. Product samples were withdrawn periodically from a high pressure sample port and analyzed using a gas chromatograph equipped with a Petrocol DH 100 m column as in Application Example 1

Figure 11:
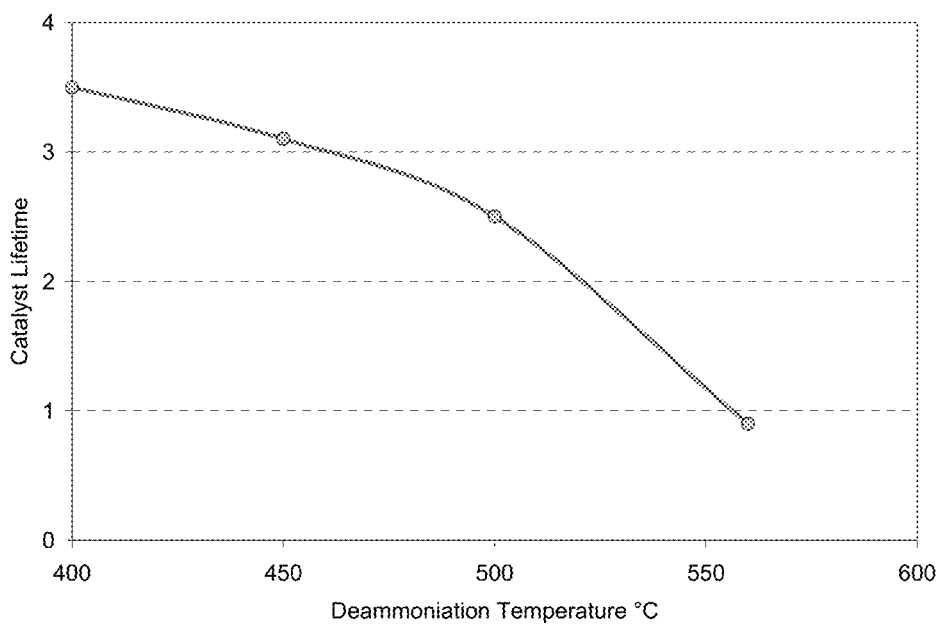
FIG. 11: Catalyst lifetime for β zeolite deammoniated at different temperatures (catalysts M-P).

FIG. 11 shows catalyst lifetime as a function of deammoniation temperature for these β catalysts. The highest performance is for the β catalyst deammoniated at 400° C. with dry air. Thus, we observed the surprising result that the deammoniation temperature (450° C. to 40° C., preferably 425° C. to 40° C.) resulted in superior catalyst lifetimes. This was a very surprising result since it had been reported that activation at 45° C. under dry conditions resulted in "barely active catalysts" and that a temperature of 55° C. was required for significantly improved activity. See Kunkeler et al., "Zeolite Beta: The Relationship between Calcination Procedure, Aluminum Configuration, and Lewis Acidity"

Application Example 7

Figure 12:
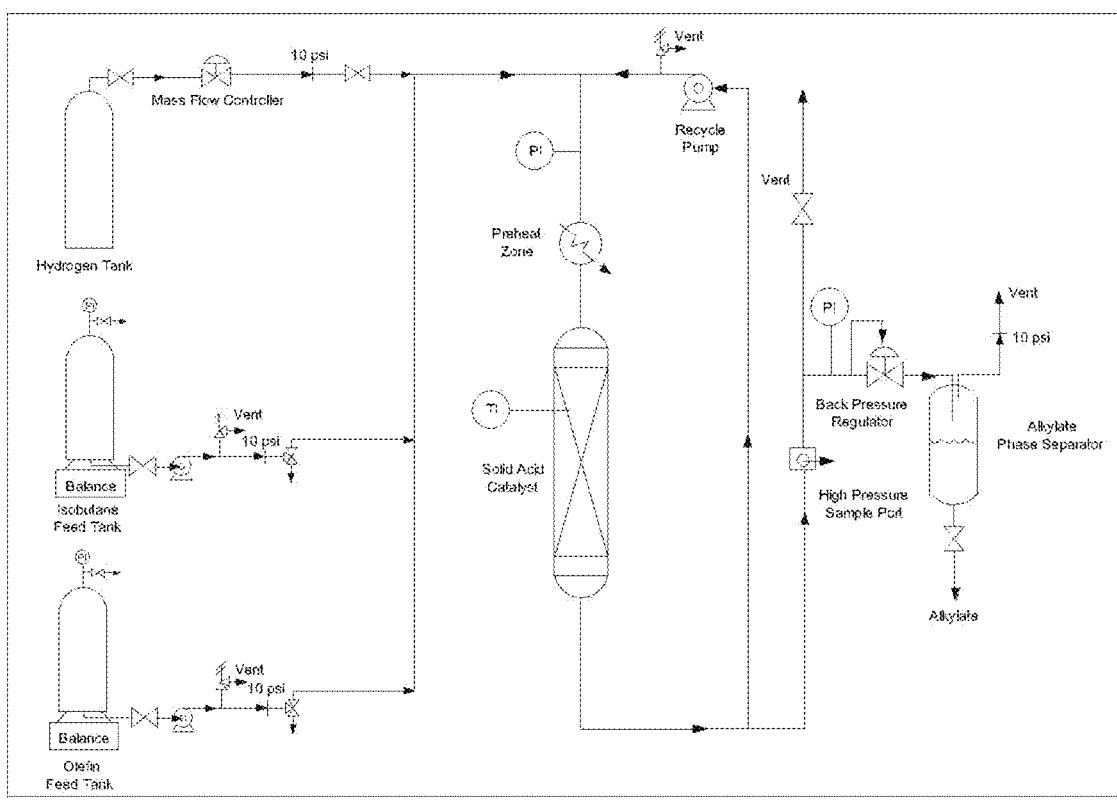
FIG. 12: Single stage feed recycle reactor schematic.

The lanthanum exchanged X zeolite from Example 4 (Catalyst D) was loaded into a fixed-bed reactor with product recycle shown in FIG. 12. A reaction feed mixture, with a I/O molar ratio of 10 (with n-butene as olefin), was fed to a bench-scale reactor with an OHSV of 0.1 $hr^{-1}$ at a temperature of 60° C. and a pressure of 300 psig. This recycle flow rate was established such that the recycle ratio was 50. Product samples were withdrawn periodically from a high pressure sample port and analyzed using a gas chromatograph equipped with a Petrocol DH 100 m column.

Figure 13:
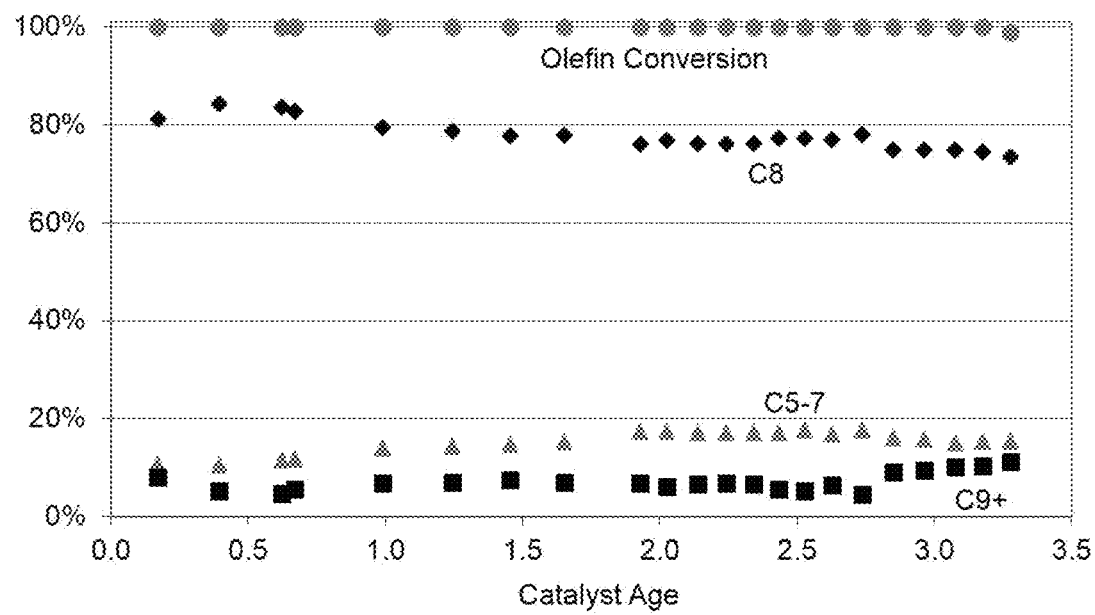
FIG. 13: Representative recycle solid-acid alkylation experimental results for Catalyst D.

FIG. 13 shows representative product distribution data using catalyst D from Example 4.

Figure 14:
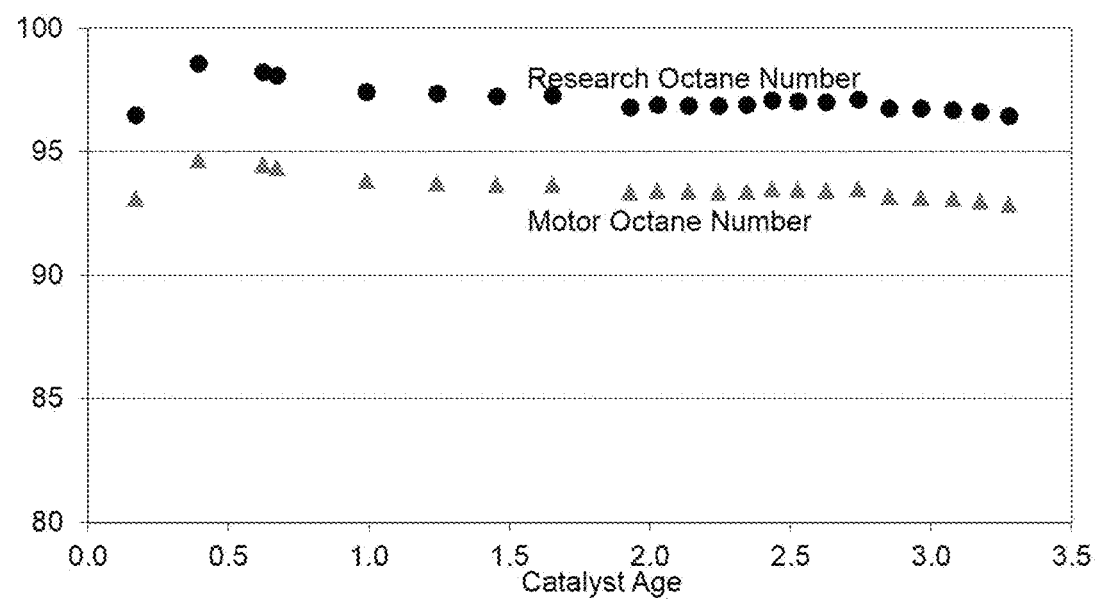
FIG. 14: Representative Octane numbers for recycle solid-acid alkylation using Catalyst D.

FIG. 14 shows reaction octane numbers as a function of run time. Research Octane Number (RON) and Motor Octane Number (MON) are calculated for the alkylate from product analysis.

The lifetime of this catalyst was >3.25 under commercial reaction conditions before regeneration. The steady state product $C_8$ selectivity was 79 wt %, RON was 97 and the product MON was 93.

Application Example 8

Figure 15:
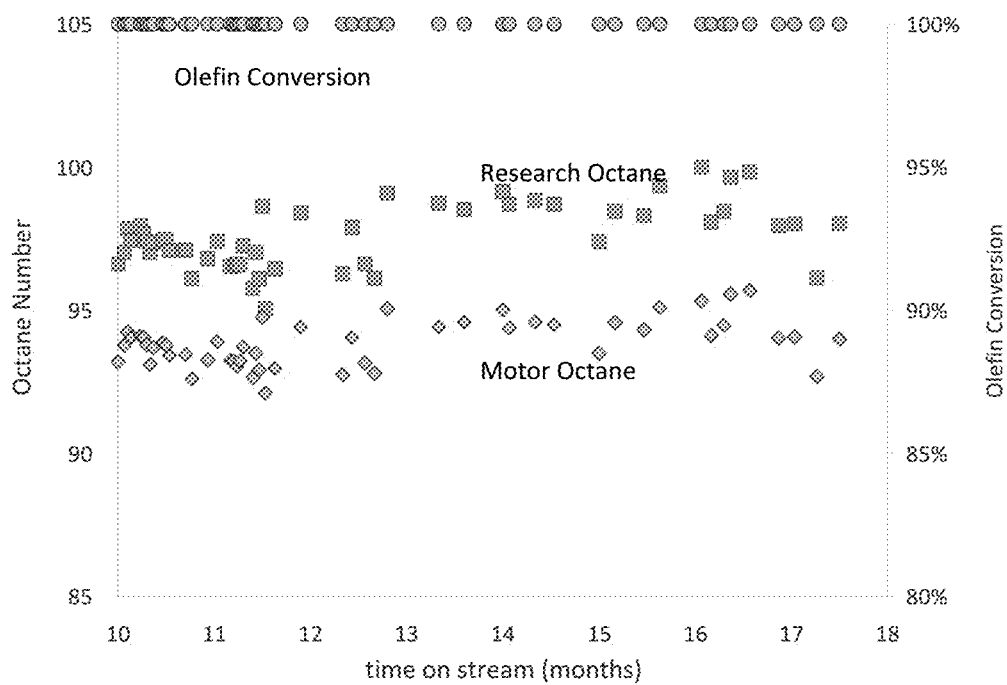
FIG. 15: Long term stability data results for Catalyst W.

The lanthanum exchanged X zeolite from Example 23 (Catalyst Z) was loaded into a fixed-bed reactor with product recycle shown in FIG. 15. A reaction feed mixture, with a I/O molar ratio of 10 (with MTBE raffinate as olefin), was fed to a bench-scale reactor with an OHSV of 0.1 $hr^{-1}$ at a temperature of 45° C. and a pressure of 300 psig. The catalyst test was run for 24 hours and then regenerated with hydrogen gas at 250° C. for 2 hours. This cycle was repeated for 18 months. Results of this test are shown in FIG. 15.

Data shown in FIG. 15 demonstrates that 0.1 wt % Platinum loading on the catalyst is adequate for regeneration the catalyst with hydrogen gas.

Application Example 9

Figure 16:
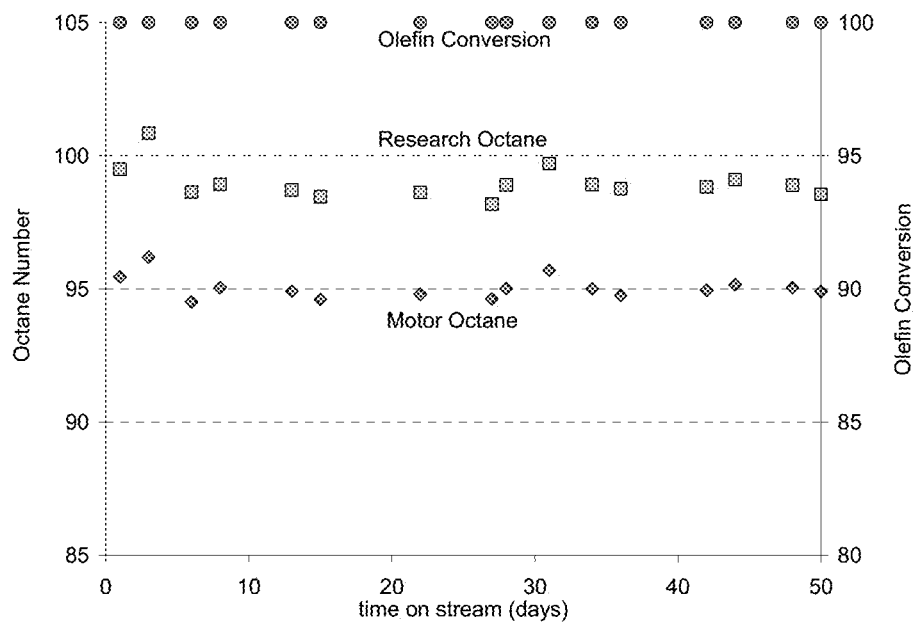
FIG. 16: Long term stability data results for Catalyst X.

The lanthanum exchanged X zeolite from Example 27 (Catalyst AA) was loaded into a fixed-bed reactor with product recycle shown in FIG. 16. A reaction feed mixture, with a I/O molar ratio of 10 (with MTBE raffinate as olefin), was fed to a bench-scale reactor with an OHSV of 0.1 hr-1 at a temperature of 45° C. and a pressure of 300 psig. The catalyst test was run for 24 hours and then regenerated with hydrogen gas at 250° C. for 2 hours. This cycle was repeated for 50 days.

The data shown in FIG. 16 demonstrates that about 0.25 wt % Nickel loading on the catalyst is adequate for regeneration the catalyst with hydrogen gas; a preferred range is 0.1 to 0.5 wt % Ni.

Application Example 10

The β zeolites were prepared with different Silica-to-Alumina Ratios (SAR) and deammoniation temperatures as in Examples 17-20 (Catalysts Q-T) and loaded into a fixed-bed reactor with product recycle shown in FIG. 14. The reaction feed mixture, I/O Ratio of 15, was fed to the reactor at a rate of 10 g/hr. The recycle stream flow rate was 40 g/hr. The combined feed rate to the reactor was 50 g/hr with an OHSV of 0.2 hr-1. Product samples were withdrawn periodically from a high pressure sample port and analyzed using a gas chromatograph equipped with a Petrocol DH 100 m column as in Application Example 1.

Figure 17:
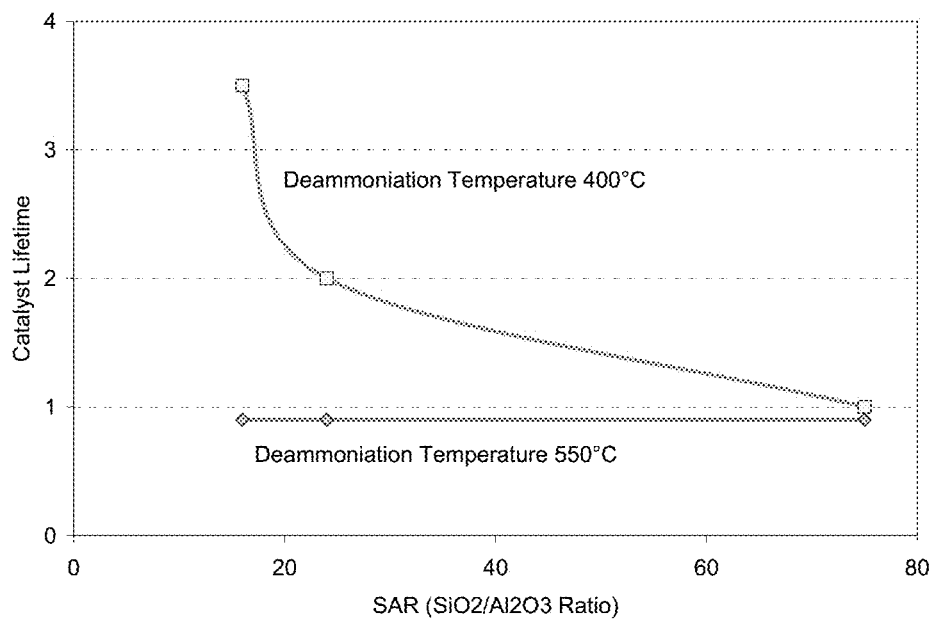
FIG. 17 shows catalyst lifetime as a function of deammoniation temperature and SAR for β zeolite catalysts.

FIG. 17 shows catalyst lifetime as a function of deammoniation temperature and SAR for these β catalysts. The highest performance is for the β catalyst at SAR 16 and deammoniated at 400° C. Results shown in FIG. 17 are unique in the way the NH4+ form is converted to the H+ form. The typical deammoniation temperature used for zeolites is typically 550° C. or higher. Our results clearly show a much superior performance at lower deammoniation temperatures.

Application Example 11

The Y zeolites were prepared without Lanthanum exchange steps followed by deammoniation as in Examples 6 (Catalysts F). The experimental conditions are identical to those of Application Example 1

Figure 18:
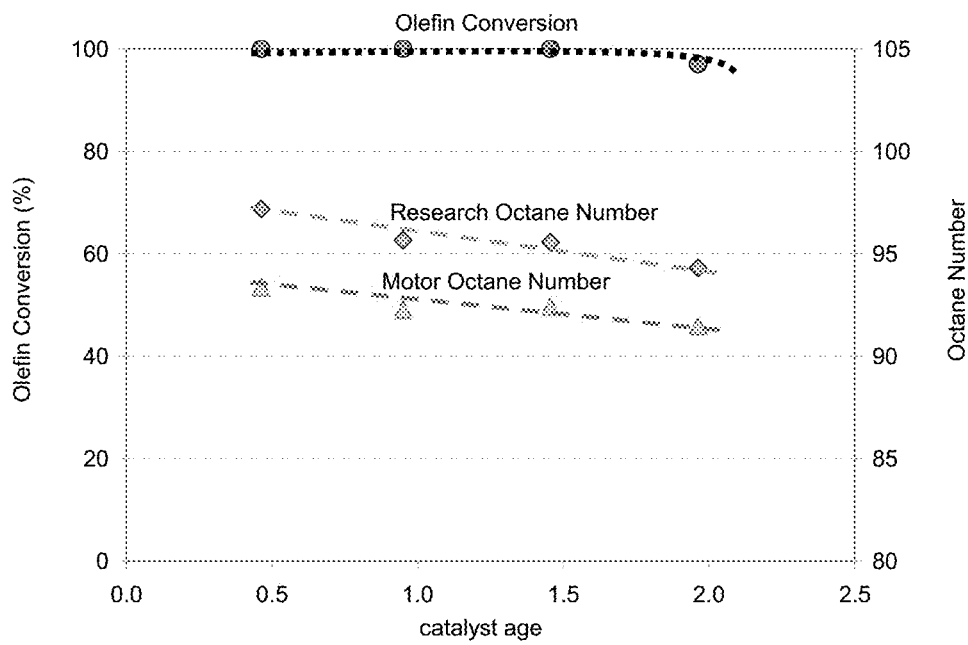
FIG. 18. Butene conversion and product octane as a function of catalyst age for the Y zeolite deammoniated at 400° C. (Catalyst F).

FIG. 18 shows butene conversion and product octane as a function of catalyst age for the Y zeolite deammoniated at 400° C. (Catalyst F)—showing superior catalyst lifetime for deammoniation at this temperature.

Comparing performance of Y-zeolite deammoniated at 400° C. (Catalyst F) with Y-zeolite deammoniated at 550° C. (catalyst G) clearly demonstrates the superiority of the low temperature deammoniation method.

It is to be understood, however, that the scope of the present invention is not to be limited to the specific embodiments described above. The invention may be practiced other than as particularly described and still be within the scope of the accompanying claims.

What is claimed is:

1. A solid-acid alkylation catalyst, comprising:
a zeolite structure comprising sodalite cages and supercages, a Si/Al molar ratio of 20 or less, less than 0.5 weight percent alkali metals, rare earth elements in the range of 10 to 35 wt %; and characterizable by a Catalyst Lifetime of 2 or greater where the Catalyst Lifetime parameter is defined as the catalyst age when olefin conversion falls below 90% using a test reaction where the solid-acid catalyst is loaded in a fixed-bed reactor such that the dT/dP>10 (diameter of tube to diameter of catalyst particles) and L/dP>50 (length of catalyst bed to diameter of catalyst particles) and exposed to a flow comprising a feed of 10:1 molar ratio of isobutane:n-butenes at 60° C. and 300 psig with a recycle ratio (R=volumetric flow rate of recycle stream/volumetric flow rate of feed stream) of 50, wherein the n-butenes comprise the olefin, where VS/VC is 7 (the ratio of system volume to catalyst volume), without regeneration of the solid-acid alkylation catalyst, and wherein a product of the test reaction has a RON of at least 92.

2. The solid-acid alkylation catalyst of claim 1 wherein the catalyst comprises 0.1 wt % to 5 wt % of an element selected from the group consisting of Pt, Pd, Ni, and combinations thereof.

3. The solid-acid alkylation catalyst of claim 1 having a catalyst lifetime of between 2.5 and 3.5.

4. The solid-acid alkylation catalyst of claim 1 where the Catalyst Lifetime parameter is defined as the catalyst age when olefin conversion falls below 95% using a test reaction where the solid-acid catalyst is loaded in a fixed-bed reactor such that the dT/dP>10 (diameter of tube to diameter of catalyst particles) and L/dP>50 (length of catalyst bed to diameter of catalyst particles) and exposed to a flow comprising a feed of 10:1 molar ratio of isobutane:n-butenes at 60° C. and 300 psig with a recycle ratio (R=volumetric flow rate of recycle stream/volumetric flow rate of feed stream) of 50, wherein the n-butenes comprise the olefin, where VS/VC is 7 (the ratio of system volume to catalyst volume), without regeneration of the solid-acid alkylation catalyst, and wherein a product of the RON of a product of the test reaction has a product is at least 92.

5. The solid-acid alkylation catalyst of claim 1 wherein the Catalyst Lifetime is 2.5 or greater.

6. A solid-acid alkylation catalyst, comprising:

a zeolite structure comprising sodalite cages and supercages, a Si/Al molar ratio of 20 or less, less than 0.5 weight percent alkali metals, rare earth elements wherein the molar ratio of rare earth elements to (Si and Al) is in the range of 0.06 to 0.20; and characterizable by a Catalyst Lifetime of 2 or greater where the Catalyst Lifetime parameter is defined as the catalyst age when olefin conversion falls below 90% using a test reaction where the solid-acid catalyst is loaded in a fixed-bed reactor such that the dT/dP>10 (diameter of tube to diameter of catalyst particles) and L/dP>50 (length of catalyst bed to diameter of catalyst particles) and exposed to a flow comprising a feed stream comprising 100:1 molar ratio of isobutane:n-butenes, wherein the n-butenes comprise the olefin, at 60° C. and 300 psig without regeneration of the solid-acid alkylation catalyst, and wherein a product of the test reaction has a RON of at least 92.

7. The solid-acid alkylation catalyst of claim 6 wherein the catalyst comprises 0.1 wt % to 5 wt % of an element selected from the group consisting of Pt, Pd, Ni, and combinations thereof.

8. The solid-acid alkylation catalyst of claim 6 having a catalyst lifetime of between 2.5 and 3.5.

9. The solid-acid alkylation catalyst of claim 6 wherein the Catalyst Lifetime is 2.5 or greater.

* * * * *